US009663419B2

(12) United States Patent
Keusenkothen et al.

(10) Patent No.: US 9,663,419 B2
(45) Date of Patent: *May 30, 2017

(54) HYDROCARBON CONVERSION PROCESS

(75) Inventors: Paul F. Keusenkothen, Houston, TX (US); Frank Hershkowitz, Basking Ridge, NJ (US); Robert D. Denton, Bellaire, TX (US); Gary D. Mohr, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 371 days.

This patent is subject to a terminal disclaimer.

(21) Appl. No.: 13/994,433

(22) PCT Filed: Dec. 20, 2011

(86) PCT No.: PCT/US2011/066165
§ 371 (c)(1),
(2), (4) Date: Sep. 18, 2013

(87) PCT Pub. No.: WO2012/099672
PCT Pub. Date: Jul. 26, 2012

(65) Prior Publication Data
US 2014/0303418 A1    Oct. 9, 2014

Related U.S. Application Data

(60) Provisional application No. 61/504,611, filed on Jul. 5, 2011, provisional application No. 61/434,417, filed
(Continued)

(30) Foreign Application Priority Data

Sep. 9, 2011    (EP) .................................... 11180674

(51) Int. Cl.
*C07C 2/06*    (2006.01)
*C07C 4/06*    (2006.01)
(Continued)

(52) U.S. Cl.
CPC .................. *C07C 2/78* (2013.01); *C07C 2/06* (2013.01); *C07C 4/06* (2013.01); *C07C 5/09* (2013.01);
(Continued)

(58) Field of Classification Search
CPC ......... C07C 2/78; C07C 7/14858; C07C 5/09; C07C 2/06; C07C 7/00
(Continued)

(56) References Cited

U.S. PATENT DOCUMENTS 1,134,677 A    4/1915    Heinemann
1,860,624 A    5/1932    Sauerwein
(Continued)

FOREIGN PATENT DOCUMENTS

BE    722895    10/1968
DE    875198    4/1953
(Continued)

OTHER PUBLICATIONS

Attar, A.; Corcoran, Am. H; Gibson, G.S. "Transformation of Sulfur Functional Groups During Pyrolysis of Coal" (1976) pp. 106-117.*
(Continued)

*Primary Examiner* — Bobby Ramdhanie
*Assistant Examiner* — Aaron Pierpont

(57) ABSTRACT

The invention relates to processes for converting a mixture of hydrocarbon and sulfur-containing molecules such as mercaptans into products comprising acetylene, ethylene, and hydrogen sulfide, to processes utilizing the acetylene and ethylene resulting from the conversion, and to equipment useful for such processes.

25 Claims, 4 Drawing Sheets

Related U.S. Application Data on Jan. 19, 2011, provisional application No. 61/434,409, filed on Jan. 19, 2011, provisional application No. 61/434,413, filed on Jan. 19, 2011, provisional application No. 61/434,410, filed on Jan. 19, 2011, provisional application No. 61/434,411, filed on Jan. 19, 2011, provisional application No. 61/434,415, filed on Jan. 19, 2011, provisional application No. 61/434,419, filed on Jan. 19, 2011, provisional application No. 61/481,999, filed on May 3, 2011, provisional application No. 61/500,854, filed on Jun. 24, 2011.

(51) Int. Cl.
  *C07C 5/09* (2006.01)
  *C07C 7/00* (2006.01)
  *C07C 2/78* (2006.01)
  *C10G 50/00* (2006.01)
  *C07C 7/148* (2006.01)

(52) U.S. Cl.
  CPC ............ *C07C 7/00* (2013.01); *C07C 7/14858* (2013.01); *C10G 50/00* (2013.01); *C07C 2521/04* (2013.01); *C07C 2521/08* (2013.01); *C07C 2521/12* (2013.01); *C07C 2523/42* (2013.01); *C07C 2523/44* (2013.01); *C07C 2523/50* (2013.01); *C10G 2300/1025* (2013.01); *C10G 2300/202* (2013.01); *C10G 2300/207* (2013.01); *C10G 2400/20* (2013.01); *C10G 2400/22* (2013.01); *C10G 2400/24* (2013.01)

(58) Field of Classification Search
  USPC .................................... 585/325, 324, 330
  See application file for complete search history.

(56) References Cited

U.S. PATENT DOCUMENTS

| | | | |
|---|---|---|---|
| 2,221,658 A | 11/1940 | Waterman et al. | |
| 2,319,679 A | 5/1943 | Hasche et al. | |
| 2,678,339 A | 5/1954 | Harris | |
| 2,692,819 A | 10/1954 | Hasche et al. | |
| 2,822,285 A | 2/1958 | Pitrot et al. | |
| 3,024,094 A | 3/1962 | Coberly | |
| 3,093,697 A | 6/1963 | Kasbohm et al. | |
| 3,156,733 A | 11/1964 | Happel et al. | |
| 3,242,223 A | 3/1966 | Nonnenmacher et al. | |
| 3,419,632 A | 12/1968 | Sogawa et al. | |
| 3,617,495 A | 11/1971 | Zimmerman, Jr. et al. | |
| 3,644,555 A | 2/1972 | Nagy et al. | |
| 3,839,484 A | 10/1974 | Zimmerman, Jr. et al. | |
| 4,274,841 A | 6/1981 | Andresen et al. | |
| 5,675,041 A | 10/1997 | Kiss et al. | |
| 5,856,592 A | 1/1999 | Hagen | |
| 6,049,011 A | 4/2000 | Kiss et al. | |
| 6,121,503 A | 9/2000 | Janssen et al. | |
| 6,177,600 B1 | 1/2001 | Netzer | |
| 6,210,561 B1 | 4/2001 | Bradow et al. | |
| 6,307,093 B1 | 10/2001 | Godwin et al. | |
| 6,578,378 B2 | 6/2003 | Kaiser et al. | |
| 7,045,670 B2 | 5/2006 | Johnson et al. | |
| 7,115,789 B2 | 10/2006 | Kuechler et al. | |
| 7,119,240 B2 | 10/2006 | Hall et al. | |
| 7,138,047 B2 | 11/2006 | Stell et al. | |
| 7,208,647 B2 | 4/2007 | Peterson et al. | |
| 7,491,250 B2 | 2/2009 | Hershkowitz et al. | |
| 7,544,852 B2 | 6/2009 | Stell et al. | |
| 7,815,873 B2 | 10/2010 | Sankaranarayanan et al. | |
| 7,846,401 B2 | 12/2010 | Hershkowitz et al. | |
| 7,943,808 B2 | 5/2011 | Hershkowitz et al. | |
| 8,158,837 B2 | 4/2012 | Mamadov et al. | |
| 8,440,070 B2 | 5/2013 | Keusenkothen | |
| 2002/0000085 A1 | 1/2002 | Hall et al. | |
| 2002/0098430 A1 | 7/2002 | Kawamura et al. | |
| 2004/0002553 A1 | 1/2004 | Hall et al. | |
| 2004/0192982 A1 | 9/2004 | Kuechler et al. | |
| 2006/0110305 A1* | 5/2006 | Van De Graaf | 423/244.04 |
| 2007/0090018 A1 | 4/2007 | Keusenkothen et al. | |
| 2007/0090019 A1 | 4/2007 | Keusenkothen et al. | |
| 2007/0090020 A1 | 4/2007 | Buchanan et al. | |
| 2007/0191664 A1* | 8/2007 | Hershkowitz et al. | 585/539 |
| 2007/0278136 A1* | 12/2007 | Stauffer | 208/189 |
| 2008/0142049 A1 | 6/2008 | Onishi et al. | |
| 2008/0300438 A1 | 12/2008 | Keusenkothen et al. | |
| 2010/0130803 A1 | 5/2010 | Keusenkothen et al. | |
| 2010/0292523 A1 | 11/2010 | Hershkowitz et al. | |

FOREIGN PATENT DOCUMENTS

| | | |
|---|---|---|
| DE | 1270537 | 6/1968 |
| DE | 2354217 | 5/1975 |
| EP | 1288182 | 3/2003 |
| EP | 1741691 | 1/2007 |
| EP | 2022772 | 2/2009 |
| GB | 795688 | 5/1958 |
| GB | 834419 | 5/1960 |
| GB | 846679 | 8/1960 |
| GB | 1007423 | 10/1965 |
| GB | 1090983 | 11/1967 |
| WO | 2005/097948 | 10/2005 |
| WO | 2011/008389 | 1/2011 |
| WO | 2012/099679 | 7/2012 |

OTHER PUBLICATIONS

Haynes, W.M. "CRC Handbook of Chemistry and Physics" 95th Ed. Internet Version 2015 (ch. 3, pp. 2-553; ch. 4, pp. 43-101).*
Energy Fuels, 2007, 21(2), pp. 640-645.
Watt, L., "The Production of Acetlene from Methane by Partial Oxidation", Thesis University OG British Columbia, Sep. 1, 1951, pp. 1-50.
SRI Consulting Process Economics Program "Acetylene" Report 16 (1966) and 16A (1982).

* cited by examiner

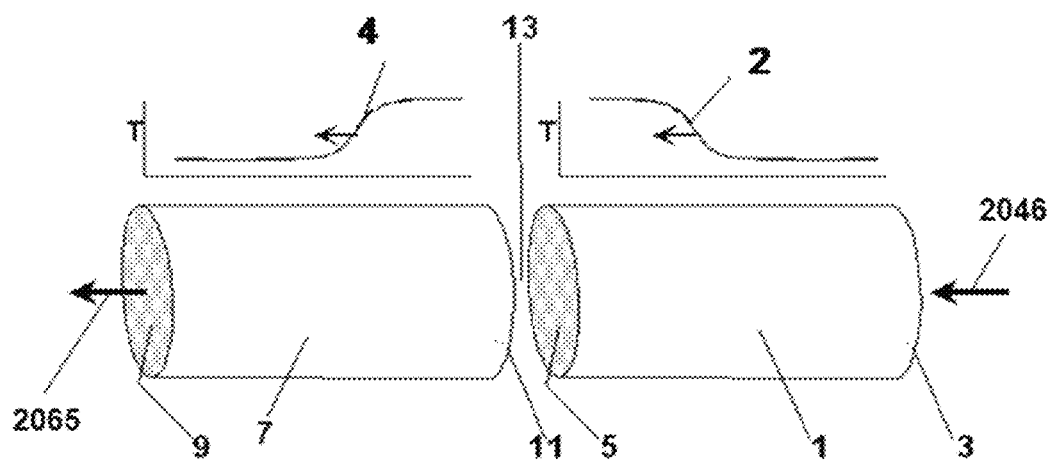
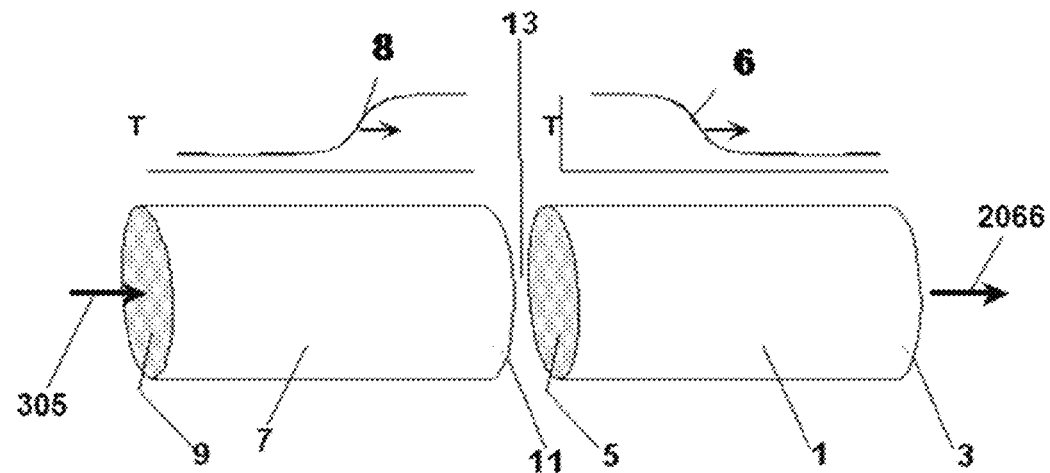

HYDROCARBON CONVERSION PROCESS

CROSS-REFERENCE TO RELATED APPLICATIONS

This application claims priority from (i) U.S. Provisional Application Ser. No. 61/504,611, filed Jul. 5, 2011, EP Application No. 11180674.1, filed Sep. 9, 2011, and PCT/US2011/066165, filed Dec. 20, 2011; (ii) U.S. Provisional Application Ser. No. 61/434,409, filed Jan. 19, 2011, and PCT/US2011/066216, filed Dec. 20, 2011; (iii) U.S. Provisional Application Ser. No. 61/434,410, filed Jan. 19, 2011, and PCT/US2011/066202, filed Dec. 20, 2011; (iv) U.S. Provisional Application Ser. No. 61/434,411, filed Jan. 19, 2011, and PCT/US2011/066210, filed Dec. 20, 2011; (v) U.S. Provisional Application Ser. No. 61/434,413, filed Jan. 19, 2011, and PCT/US2011/066196, filed Dec. 20, 2011; (vi) U.S. Provisional Application Ser. No. 61/434,415, filed Jan. 19, 2011, and PCT/US2011/066152, filed Dec. 20, 2011; (vii) U.S. Provisional Application Ser. No. 61/434,417, filed Jan. 19, 2011, and PCT/US2011/066186, filed Dec. 20, 2011; (viii) U.S. Provisional Application Ser. No. 61/434,419, filed Jan. 19, 2011, and PCT/US2011/066206, filed Dec. 20, 2011; (ix) U.S. Provisional Application Ser. No. 61/481,999, filed May 3, 2011, and PCT/US2011/066180, filed Dec. 20, 2011; (x) U.S. Provisional Application Ser. No. 61/500,854, filed Jun. 24, 2011, and PCT/US2011/066174, filed Dec. 20, 2011, the contents of each of which are incorporated by reference in their entirety.

FIELD

The invention relates to processes for converting a mixture of hydrocarbon and sulfur-containing molecules such as mercaptans into products comprising acetylene, ethylene, and hydrogen sulfide, to processes utilizing the acetylene and ethylene resulting from the conversion, and to equipment useful for such processes.

BACKGROUND

Saturated hydrocarbon can be converted to unsaturated products such as acetylene and/or ethylene by pyrolysis reactions. One such pyrolysis reaction, steam cracking, can be used to produce acetylene and ethylene from hydrocarbon mixtures having a relatively broad molecular weight range, such as mixtures comprising hydrocarbon having a carbon number from about $C_2$ to about $C_{20}$, (e.g., ethane, naphtha, diesel, gas oil, etc.). Higher temperature pyrolysis, e.g., at a temperature≥1200° C., can be used to produce acetylene and ethylene from methane.

Hydrocarbon source materials, e.g., crude oil and natural gas, generally have a significant heteroatom content, e.g., in the form of sulfur-containing, oxygen-containing, and nitrogen-containing molecules. In conventional pyrolysis processes, these are removed upstream of the pyrolysis in order to prevent contamination of the hydrocarbon product. This removal can be difficult to accomplish, particularly for sulfur-containing molecules when these are present in relatively high concentration. Some of the difficulties involved in removing sulfur-containing molecules upstream of pyrolysis result from the wide distribution of the molecules' molecular weights, chemical bonding characteristics, atmospheric boiling points, etc.

For sources of liquid hydrocarbon containing both hydrogen sulfide and mercaptans, two separations are generally required: a first separation for removing hydrogen sulfide, e.g., by stripping; and a second separation for removing mercaptans, e.g., by caustic extraction. For sources of hydrocarbon in the vapor phase, an amine contactor is generally utilized for removing hydrogen sulfide, with mercaptans being removed by caustic extraction. There is a need for improved pyrolysis processes having fewer sulfur-removal steps, particularly for processes that have the flexibility to locate the sulfur removal either upstream or downstream of the pyrolysis.

SUMMARY

The invention relates to a method for treating natural gas, comprising
(a) providing a first mixture comprising ≥90.0 wt. % of natural gas, the natural gas comprising ≥1.0 wt. % methane, ≥1.0 ppmw hydrogen sulfide, and ≥4.0 ppmw mercaptans based on the weight of the natural gas;
(b) exposing the first mixture under thermal pyrolysis conditions to a temperature sufficient for converting (i) ≥10.0 wt. % of the first mixture's methane to unsaturated hydrocarbon and molecular hydrogen, based on the weight of the methane in the first mixture, and (ii) ≥90.0 wt. % of the first mixture's mercaptans to non-mercaptan, non-thiophenic sulfur based on the weight of the first mixture, to produce a second mixture comprising ≥1.0 ppmw hydrogen sulfide and ≥1.0 wt. % $C_2$ unsaturates based on the weight of the second mixture; and
(c) separating at least a portion of the hydrogen sulfide from the second mixture; wherein the natural gas is provided to the first mixture with no intervening mercaptans-removal steps.

In another embodiment, the invention relates to a methane conversion process, comprising:
(a) providing a first mixture comprising ≥90.0 wt. % methane and ≥4.0 ppmw mercaptans based on the weight of the first mixture; and
(b) exposing the first mixture under thermal pyrolysis conditions to a temperature sufficient for converting (i) ≥10.0 wt. % of the first mixture's methane to unsaturated hydrocarbon based on the weight of the methane in the first mixture, and (ii) ≥90.0 wt. % of the first mixture's mercaptans to non-mercaptan, non-thiophenic sulfur compounds based on the weight of the first mixture to produce a second mixture comprising ≥1.0 wt. % $C_2$ unsaturates based on the weight of the second mixture.

In yet another embodiment, the invention relates to a hydrocarbon conversion process, comprising:
(a) providing a first mixture comprising ≥0.5 wt. % hydrocarbon and ≥4.0 ppmw mercaptans based on the weight of the first mixture; and
(b) exposing a first mixture to a temperature≥$1.20 \times 10^{3}$° C. in a first region under pyrolysis conditions to convert at least a portion of the hydrocarbon and ≥90.0 wt. % of the first mixture's mercaptans based on the weight of mercaptans in the first mixture to produce a second mixture, the second mixture comprising ≥1.0 wt. % $C_2$ unsaturates, ≤20.0 wt. % $CO_x$, wherein x is 1 or 2, and ≤1.0 ppmw thiophene based on the weight of the second mixture.

BRIEF DESCRIPTION OF THE DRAWINGS

FIGS. 3a and 3b schematically illustrate the pyrolysis reactor's temperature profile.

DETAILED DESCRIPTION OF THE EMBODIMENTS

Figure 1:
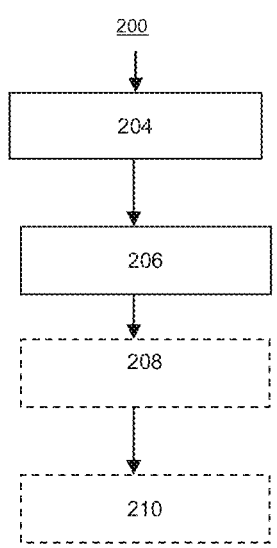
FIG. 1 schematically illustrates embodiments of the invention relating to the thermal pyrolysis of a first mixture comprising hydrocarbon and mercaptans. Optional stages of the process are enclosed in dashed rectangles.

The invention relates to the conversion of mixtures comprising hydrocarbon and 4.0 ppmw mercaptans based on the weight of the mixture. It has been found that exposing such a mixture to a temperature≥1200° C. (which as used herein means $1.20 \times 10^{3\circ}$ C., i.e., three significant digits) under pyrolysis conditions converts (i) at least a portion of the mixture's hydrocarbon to unsaturated hydrocarbon, and (ii) ≥90.0 wt. % of the mixture's mercaptans, e.g., to hydrogen sulfide and methane, without producing a significant amount of thiophene or $CO_x$ wherein x≥1.0, e.g., x=1 or 2. This discovery leads to a considerable simplification in processing hydrocarbon mixtures comprising mercaptans. In a conventional pyrolysis process, a first feed separation is utilized for removing hydrogen sulfide and at least one additional feed separation is utilized for removing mercaptans, the first and second separations being upstream of the pyrolysis. The process of the invention is more efficient in that it utilizes one sulfur removal stage (a hydrogen sulfide separation step) downstream of high-temperature thermal pyrolysis instead of two sulfur removal stages upstream of the pyrolysis, one stage for removing hydrogen sulfide, and a second stage for removing mercaptans. Unlike partial oxidation, which utilizes oxygen as a reactant, the process of the invention does not require introducing additional heteroatoms (such as nitrogen and/or oxygen) which would otherwise need to be separated from the unsaturated hydrocarbon products downstream of the pyrolysis.

The process generally involves exposing a first mixture to a temperature≥$1.20 \times 10^{3\circ}$ C. under thermal pyrolysis conditions, the first mixture comprising saturated hydrocarbon and ≥4.0 ppmw mercaptans based on the weight of the first mixture. The thermal pyrolysis converts the first mixture to a second mixture comprising $C_2$ unsaturates and non-mercaptan, non-thiophenic sulfur compounds such as hydrogen sulfide.

In embodiments where the second mixture's enthalpy is greater than that of the first mixture, the process of producing the second mixture from the first mixture can involve abstracting heat from the first region, e.g., from reactor components contained therein. Optionally, at least a portion of the abstracted heat is produced by partially or completely oxidizing (e.g., combusting) at least a portion of a fourth mixture comprising oxidizable atoms and molecules (e.g., CO, hydrogen, hydrocarbon, etc.), the oxidizing occurring in a second region that is at least partially coextensive with the first region. A fifth mixture, derived from the fourth mixture and comprising, e.g., products formed by oxidizing at least a portion of the fourth mixture, can be conducted away from the second region.

The process can further comprise upgrading the second mixture by removing at least a portion of the second mixture's hydrogen sulfide, e.g., by extraction, absorption, adsorption, stripping, etc. For example, the process can comprise deriving a third mixture from the second mixture, wherein (a) the second mixture comprises unsaturated hydrocarbon, molecular hydrogen, and ≥6.0 ppmw hydrogen sulfide based on the weight of the second mixture; and (b) the third mixture comprises unsaturated hydrocarbon, molecular hydrogen, and <1.0 ppmw hydrogen sulfide based on the weight of the third mixture.

The process can further comprise converting at least a portion of the third mixture's acetylene to form a first product comprising, e.g., ethylene. For example, the conversion can be a catalytic conversion that is conducted at least partially in the vapor or liquid phase and the catalyst comprises at least one element selected from Group VIII of the Periodic Table. In an embodiment, the process further comprises polymerizing at least a portion of the product.

For the purpose of this description and appended claims, the following terms are defined. The term "hydrocarbon" means molecules (and mixtures thereof) including both carbon atoms and hydrogen atoms, and optionally including other atoms (heteroatoms), such as oxygen, sulfur, and nitrogen, wherein the carbon atoms and hydrogen atoms together comprise ≥75.0% of the atoms present in the molecule or mixture of molecules. The term oxygenate means molecules that contain at least one oxygen atom, but excluding hydrocarbon, e.g., $H_2O$, CO, $CO_2$, etc. The term "molecular hydrogen" means $H_2$. The term molecular oxygen means $O_2$.

The "Periodic Table of the Elements" means the Periodic Chart of the Elements as tabulated on the inside cover of The Merck Index, 12th Edition, Merck & Co., Inc., 1996.

The terms "convert", "conversion", "converting", etc., with respect to pyrolysis processes include, e.g., any molecular decomposition, cracking, breaking apart, reformation of molecules, including hydrocarbon, oxygenate, etc., by at least pyrolysis heat. With respect to non-pyrolysis processes that are at least partly catalytic, the term conversion includes, e.g., hydroprocessing (such as hydrogenation, hydrotreating, etc.), hydroformylation, catalytic separation, etc.

The terms "pyrolysis" and "pyrolysis chemistry" mean an endothermic reaction conducted at a temperature sufficient for thermally breaking C—C or C—H bonds, optionally aided by a catalyst, e.g., the conversion of hydrocarbons to unsaturates such as ethylene and acetylene.

The term "pyrolysis reactor", as used herein, refers to a reactor, or combination or system thereof for converting hydrocarbons by at least pyrolysis. A pyrolysis reactor optionally includes one or more reactors and/or associated equipment and lines. The term pyrolysis reactor encompasses, e.g., the combination and system of first and second pyrolysis reactors described in U.S. Pat. No. 7,943,808. With respect to pyrolysis reactors, the term "residence time" means the average time duration for non-reacting (non-converting by pyrolysis) molecules (such as He, $N_2$, Ar) having a molecular weight in the range of 4 to 40 to traverse a pyrolysis region of a pyrolysis reactor. The term "pyrolysis stage" means at least one pyrolysis reactor, and optionally means for conducting one or more feeds thereto and/or one or more products away therefrom. With respect to reactors, the term "region" means a location within a reactor, e.g., a specific volume within a reactor, a specific volume between two reactors and/or the combination of different disjointed volumes in one or more reactors. A "pyrolysis region" is a region for conducting pyrolysis. The term "thermal pyrolysis" means <50.0% of the heat utilized by the pyrolysis is provided by (a) exothermically reacting the pyrolysis feed, e.g., by exothermically reacting an oxidant with hydrocarbon and/or hydrogen in the pyrolysis feed and/or (b) contacting the pyrolysis feed with the gaseous and/or liquid products of combustion to heat the pyrolysis feed. For example, in thermal pyrolysis≥50.0% of the heat utilized by the pyrolysis is provided by heat transfer from reactor components, e.g., solid surfaces associated with a pyrolysis reactor; optionally 80.0% or ≥90.0% of the heat utilized by the pyrolysis is provided by such heat transfer. The term "thermal pyrolysis reactor" means a pyrolysis reactor wherein ≥50.0% of the heat utilized by the pyrolysis is provided by heat transfer from reactor components, e.g., solid surfaces associated with the reactor such as tubulars or bed materials; optionally ≥80.0% or 90.0% of the heat utilized by the pyrolysis is provided by such heat transfer. Optionally, exothermic oxidation, e.g., combustion, occurs within the thermal pyrolysis reactor.

The term "high-severity" with respect to pyrolysing a pyrolysis feed such as the first mixture means pyrolysis conditions resulting in the conversion of the mixture to make a product having an acetylene content≥10.0 wt. % based on the weight of the hydrocarbons in the pyrolysis feed. The operating conditions for a thermal pyrolysis reactor may be characterized by a severity threshold temperature that divides low-severity operating conditions in thermal pyrolysis reactors from high-severity operating conditions in thermal pyrolysis reactors. The severity threshold temperature is defined as the lowest temperature at which the feed to the reactor may react at a residence time≤0.1 second to make at least 10.0 wt. % acetylene as a percent of the hydrocarbons in the mixture evaluated at the given operating conditions of the process. The high-severity operating conditions for a thermal pyrolysis reactor may be characterized as peak pyrolysis gas temperatures that are greater than the severity threshold temperature. The low-severity thermal pyrolysis reactor may be characterized as pyrolysis gas temperatures that are less than the severity threshold temperature and no pyrolysis gas temperatures that exceed the severity threshold temperature. For example, for the thermal conversion of a methane feed at a pressure of 14.7 psig (101 kPa) and with 2:1 molar ratio of molecular hydrogen to methane, the threshold temperature is about 1274° C. for this process. At temperatures at or above 1274° C., yields of acetylene can exceed 10.0 wt. % of feed methane, at some time≤0.1 seconds. Conversely, at temperatures below 1274° C., there are no times≤0.1 seconds for which yields of acetylene reach 10.0 wt. % of the methane.

The term "peak pyrolysis gas temperature" means the maximum temperature achieved by the bulk pyrolysis stream gases as they travel through the pyrolysis reactor (e.g., a cracking region or radiant region). One skilled in the art will appreciate that temperatures immediately proximate to a partition may be higher, and may, in some infinitesimal layer, actually approach the partition's temperature. However, the pyrolysis temperature referred to herein should be considered a bulk gas temperature, which is a temperature that could be measured by a device (such as a thermocouple) that is not in contact with the partition. For example, if the gas is traveling through tubulars in a thermal pyrolysis reactor, the bulk gas temperature may be taken as the average temperature over any tubular cross-section, and the peak pyrolysis gas temperature as the highest cross-sectional average temperature of the pyrolysis stream.

The second mixture is generally derived by thermal pyrolysis of the first mixture, the first mixture being derived from one or more source materials. The term "source materials" means sources comprising hydrocarbon. Examples of source materials comprising hydrocarbon include one or more of petroleum-derived streams; syngas (a mixture comprising carbon monoxide and hydrogen), methane; methane-containing streams such as coal bed methane, biogas, associated gas, natural gas, and mixtures or components thereof; synthetic crudes; shale oils; or hydrocarbon streams derived from plant or animal matter. Suitable hydrocarbon source materials include those described in U.S. Pat. Nos. 7,943,808 and 7,544,852, which are incorporated by reference herein in their entirety.

Optionally, one or more mixtures and/or source materials comprises hydrogen atoms. The term "hydrogen content" of a mixture or source material means atomic hydrogen bound to carbon and/or heteroatoms covalently bound thereto and which excludes molecular hydrogen ($H_2$) in the mixture (or source material) expressed as a weight percent based on the weight of the hydrocarbons in the mixture (or source material). Optionally, one or more mixtures and/or source materials comprises non-volatiles. The term "non-volatiles" means molecules and mixtures thereof having a nominal atmospheric boiling point≥570.0° C., e.g., refractory oxygenates, refractory hydrocarbon, metals, minerals, etc. American Society of Testing and Materials ("ASTM") methods can be used to determine the nominal atmospheric boiling point (ASTM method 1078) and the amount and properties of such non-volatiles, such as ASTM methods D-6560, D-7061, D-189, D-482, D-524, and D-2415. Non-volatiles that are capable of being combusted are called "combustible non-volatiles". The term non-volatiles encompasses e.g., coke, ash, soot, resid, metal, mineral, ash-forming asphaltenic, tar, etc., including those formed, e.g., during or after oxidation (e.g., combustion or partial oxidation) and/or pyrolysis, including those which may remain as a residue or deposit in the reaction region. Optionally, one or more mixtures and/or source materials comprises $C_{3+}$. The term "$C_{3+}$" means molecules having at least three carbon atoms, including, e.g., coke and soot, whether those products emerge from the reactor or remain within the pyrolysis reactor. The term "reactor effluent" means products of pyrolysis conducted away from the reactor. The reactor effluent comprises $C_2$ unsaturates, where the term "$C_2$ unsaturates" means hydrocarbon having two carbon atoms and two or four hydrogen atoms.

Suitable reaction conditions; the first, second, third, fourth, and fifth mixtures; and related products and byproducts will now be described in more detail. Although the following embodiments are described in terms of high-temperature thermal pyrolysis reactions, the invention is not limited thereto, and this description is not meant to foreclose other embodiments within the broader scope of the invention.

I. First Mixture

The first mixture comprises hydrocarbon and ≥4.0 ppmw mercaptans based on the weight of the first mixture. Optionally, the first mixture further comprises one or more of hydrogen sulfide, molecular hydrogen, or diluent. The type of hydrocarbon is not critical; e.g., the hydrocarbon can even comprise hydrocarbon non-volatiles, including those that are not in the gas phase at the temperature, pressure, and composition conditions subsisting at the inlet to the pyrolysis reactor. The first mixture can comprise, e.g., ≥2.0 wt. % hydrocarbon, such as ≥90.0 wt. % methane based on the weight of the first mixture.

The first mixture can be derived from one or more source materials, as defined in the preceding section. Optionally, the source material has, e.g., a hydrogen content in the range of 6.0 wt. % to 25.0 wt. %, 8.0 wt. % to 20.0 wt. % (e.g., not natural gas), or 20.0 wt. % to 25.0 wt. % (e.g., natural gas). Optionally, the first mixture has a hydrogen (all hydrogen atoms in the first mixture regardless of atomic or molecular form) to carbon (all carbon atoms in the first mixture regardless of atomic or molecular form) atomic ratio in the range of from 1.0 to 15.0, e.g., in the range of from 4.0 to 8.0. In an embodiment, at least 15.0 wt. % of the first mixture's molecular hydrogen based on the weight of the first mixture is derived from the second mixture.

Optionally, the first mixture further comprises diluent, e.g., ≥1.0 wt. % of diluent based on the weight of the first mixture. Suitable diluents (which can be a diluent mixture) include one or more of nitrogen ($N_2$), oxygenate, amines, mixtures of amines, non-hydrocarbon non-volatiles (whether combustible or not) including refractory inorganics such as refractory oxygenates, inert gas (including inert gas mixtures), etc. In an embodiment, the first mixture comprises a total amount of non-combustible non-volatiles (e.g., ash; ASTM D-189), from all sources, ≤2.0 parts per million weight (ppmw) based on the weight of the first mixture, e.g., ≤1.0 ppmw. Optionally, the first mixture comprises a total amount of combustible non-volatiles (e.g., tar, asphaltenes, ASTM D-6560) in the first mixture, from all sources, ≤5 wt. % based on the weight of the hydrocarbon in the first mixture, e.g., ≤1.0 wt. %, such as ≤100.0 ppmw or ≤10.0 ppmw.

In one or more embodiments, the first mixture comprises ≥0.5 wt. % hydrocarbon, e.g., in the range of about 1.0 wt. % to about 95.0 wt. %, such as about 25.0 wt. % to about 85.0 wt. % and ≥4.0 ppmw mercaptans, or ≥10.0 ppmw, or ≥50.0 ppmw, e.g., in the range of 5.0 ppmw to $1.0 \times 10^5$ ppmw, such as 10.0 ppmw to $5.0 \times 10^3$ ppmw; the weight percents being based on the weight of the first mixture. The first mixture can comprise ≥10.0 ppmw methyl mercaptan based on the weight of the first mixture. Optionally, the first mixture further comprises at least one of ≥1.0 ppmw hydrogen sulfide, or ≥10.0 ppmw, or ≥50.0 ppmw, e.g., in the range of 2.0 ppmw to $1.0 \times 10^5$ ppmw, such as 10.0 ppmw to $5.0 \times 10^3$ ppmw; ≥0.1 wt. % molecular hydrogen, e.g., in the range of 0.5 wt. % to 35.0 wt. %, such as 1.0 wt. % to 25.0 wt. %; and ≥0.01 wt. % diluent, e.g., in the range of 0.5 wt. % to 50.0 wt. %, such as 1.0 wt. % to 10.0 wt. %, based on the weight of the first mixture. Optionally, the hydrocarbon of the first mixture comprises ≥75.0 wt. % methane, e.g., ≥90.0 wt. %, such as ≥99.0 wt. % methane, based on the weight of the first mixture's hydrocarbon. The first mixture comprises ≤5.0 wt. % of molecular oxygen based on the weight of the first mixture.

The hydrocarbon of the first mixture can be derived from natural gas (e.g., a gas of geological origin). Optionally, the first mixture comprises, consists essentially of, or consists of the natural gas, such as when the first mixture comprises ≥90.0 wt. % of a natural gas based on the weight of the first mixture. For example, the first mixture can comprise upgraded natural gas (such as natural gas that has been at least partially sweetened and/or dehydrated). Besides methane, natural gas commonly includes other hydrocarbons (such as ethane and other alkanes), generally in amounts that are less than or equal to the amount of methane in the natural gas on a weight basis. In a particular embodiment, the source material is natural gas comprising methane, ≥5.0 mg/m³ hydrogen sulfide (GPA Standard No. 2265:1968) and ≥4.0 mg/m³ mercaptans (GPA Standard No. 2265:1968) based on the volume (in cubic meters) of the natural gas. Optionally the natural gas comprises ≥1.0 wt. % of methane based on the weight of the natural gas, e.g., ≥25.0 wt. %, such as ≥50.0 wt. %. Optionally, the natural gas further comprises one or more of molecular oxygen in the range of 0.01 wt. % to 5.0 wt. %, ≥4.0 wt. % molecular nitrogen, or ≥1.0 wt. % of carbon dioxide. Optionally, the natural gas has a Wobble Index (ISO Standard 6976:1995) in the range of 35.0 MJ/m³ to 60.0 MJ/m³, e.g., in the range of 40.0 MJ/m³ to 57.0 MJ/m³, such as 45.0 MJ/m³ to 55.0 MJ/m³. Optionally, the natural gas has a specific gravity (ASTM D3588)≥0.555, e.g., in the range of 0.56 to 1.5, such as 0.57 to 0.7. A first mixture that is derived from such a natural gas can comprise, e.g., ≥20.0 wt. % methane based on the weight of the first mixture, e.g., in the range of 20.0 wt. % to 99.0 wt. %, such as 25.0 wt. % to 95.0 wt. %; ≥5.0 mg/m³ hydrogen sulfide (GPA Standard No. 2265:1968), e.g., in the range of 7.5 mg/m³ to $1.0 \times 10^4$ mg/m³, such as 10.0 mg/m³ to $1.0 \times 10^3$ mg/m³; and ≥4.0 mg/m³ mercaptans (GPA Standard No. 2265:1968), e.g., in the range of 7.5 mg/m³ to $1.0 \times 10^4$ mg/m³, such as 10.0 mg/m³ to $1.0 \times 10^3$ mg/m³; wherein (i) the methane wt. % is based on the weight of the first mixture and (ii) the hydrogen sulfide and mercaptans amounts are per cubic meter (m³) of the first mixture at 20.0° C. at 1.0 bar.

II. Process for Deriving the Second Mixture

The second mixture is produced by exposing the first mixture to a temperature≥$1.20 \times 10^3$° C. under pyrolysis conditions, e.g., high-severity thermal pyrolysis conditions. The to process is illustrated schematically in FIG. 1. The first mixture is derived from one or more source materials 200, the source materials optionally being upgraded in optional preparation stage 204. Optional preparation stage 204 can be utilized for one or more of (i) separating one or more of hydrocarbon, non-combustible nonvolatiles, mercaptans, hydrogen sulfide, molecular hydrogen, or diluent from the source material, (ii) adding one or more of hydrocarbon, molecular hydrogen, or diluent to the source material, (iii) thermally upgrading (e.g., coking or visbreaking) the source material, or (iv) catalytically upgrading (e.g., hydroprocessing, such as hydrotreating) the source material, etc. When utilized in connection with one or more of (ii)-(iv), added hydrocarbon, molecular hydrogen, or diluent can be obtained, e.g., from sources external to the process, from byproducts separated from the second or fifth mixtures, etc. Although stage 204 can include means for removing hydrogen sulfide and/or mercaptans, this is not required. In an embodiment, stage 204 does not include means for removing hydrogen sulfide and/or mercaptans.

Accordingly, the process is compatible with a first mixture that includes mercaptans and a broader range of hydrocarbon (e.g., methane, hydrocarbon with significantly lower hydrogen content than methane, high molecular weight hydrocarbon, aromatic hydrocarbon, etc.) which have not been observed to form the specified second mixture when exposed to a temperature<$1.20 \times 10^3$° C. under thermal pyrolysis conditions. In other words, the process is advantageous in that it may utilize a first mixture comprising a broad range of hydrocarbon mixtures in pyrolysis stage 206 even without upgrading in preparation stage 204 to form the specified second mixture.

The first mixture can be exposed to a temperature≥$1.20 \times 10^3$° C. in pyrolysis stage 206, the first mixture comprising hydrocarbon and ≥4.0 ppmw mercaptans based on the weight of the first mixture. The pyrolysis of the first mixture produces a second mixture comprising unsaturated hydrocarbon and molecular hydrogen; with ≥90.0 wt. %, e.g., ≥95.0 wt. %, such as ≥99.0 wt. % of the first mixture's mercaptans being converted by the pyrolysis to (i) hydrocarbon and (ii) non-thiophenic, non-mercaptans sulfur compounds in the second mixture. It has been found that the pyrolysis converts ≥1.0 wt. % of the first mixture's hydrocarbon (based on the weight of the first mixture's hydrocarbon), e.g., ≥10.0 wt. %, to unsaturated hydrocarbon in the second mixture. For example, ≥10.0 wt. % of the first mixture's methane can be converted to unsaturated hydrocarbon. It has also been found that exposing the first mixture to these conditions results in an amount of combustible non-volatile hydrocarbon (e.g., coke) in the second mixture in the range of 5.0 wt. % to 40.0 wt. % based on the weight of the second mixture, generally at least part of which is deposited as a residue in the pyrolysis stage. At least a portion of the residue can be oxidized and conducted away from the thermal pyrolysis stage during regeneration. At least a portion of the heat derived from this oxidation can be used in, e.g., the thermal pyrolysis reaction for deriving the second mixture from the first mixture.

Preparation stage 204 is optional. In other words, the first mixture can comprise (or consist essentially of, or even consist of) hydrocarbon obtained directly from source materials 200, such as natural gas comprising hydrogen sulfide and mercaptans, optionally with no intervening process steps. Following the optional preparation stage 204, the first mixture is conducted to pyrolysis stage 206 wherein it is exposed to a temperature≥$1.20 \times 10^{3}$° C. under thermal pyrolysis conditions, e.g., a temperature≥$1.40 \times 10^{3}$° C. under high-severity thermal pyrolysis conditions, to convert at least a portion of the first mixture to the second mixture. At least a first portion of the second mixture, e.g., a portion which comprises $C_2$ unsaturates, molecular hydrogen, and hydrogen sulfide, is conducted away from the pyrolysis stage, e.g., to an optional upgrading stage 208. The first portion can comprise, e.g., of one or more of hydrocarbons (such as saturated hydrocarbon and/or those containing one or more heteroatoms), diluent, non-volatiles, saturated hydrocarbons, hydrogen sulfide, molecular hydrogen, etc. It is generally desirable to expose the portion of the second mixture conducted away from stage 206 to a reduced temperature (e.g., a temperature≤300° C., e.g., ≤200° C., such as ≤100° C.) in order to prevent the reformation of mercaptans by the reaction of the second mixture's olefin and hydrogen sulfide. This cooling can be conducted in stage 208 if desired. Optionally, a second portion is separated from the second mixture, the second portion comprising, e.g., at least a portion of the second mixture's non-volatiles. For example, the second portion can comprise that portion of the second mixture that is not in the vapor phase at the downstream end of the pyrolysis reactor of stage 206. Optionally, the second portion remains in the pyrolysis stage (e.g., in the pyrolysis reactor), e.g., as coke.

Thermal pyrolysis stage 206 will now be described in more detail. Conventional pyrolysis reactors are suitable for use in stage 206, but the invention is not limited thereto. Suitable reactors include, for example, regenerative reverse flow reactors as described in U.S. Pat. No. 7,943,808 and thermal pyrolysis reactors as described in U.S. Pat. No. 7,491,250; U.S. Patent Application Ser. No. 61/349,464; and U.S. Patent App. Pub. Nos. 2007/0144940 and 2008/0142409, all of which are incorporated by reference herein in their entirety. Optionally, the thermal pyrolysis is conducted under high-severity thermal pyrolysis conditions, e.g., by exposing the first mixture to temperature in the range of about $1.40 \times 10^{3}$° C. to about $2.20 \times 10^{3}$° C., e.g., in the range of about $1.45 \times 10^{3}$° C. to about $1.80 \times 10^{3}$° C. In an embodiment, where the reactor's temperature is relatively constant over the reaction region, as may be the case when the pyrolysis reactor is a tubular reactor heated by a burner located in proximity to the outside of the tube, the first mixture achieves a peak pyrolysis gas temperature in the range of about $1.50 \times 10^{3}$° C. to about $1.675 \times 10^{3}$° C., e.g., in the range of about $1.54 \times 10^{3}$° C. to about $1.65 \times 10^{3}$° C. In embodiments where the reactor's temperature exhibits significant variation over the reaction region, as may be the case in a regenerative, reverse-flow pyrolysis reactor, the first mixture achieves a peak pyrolysis gas temperature in the range of about $1.40 \times 10^{3}$° C. to about $2.20 \times 10^{3}$° C., e.g., in the range of about $1.45 \times 10^{3}$° C. to about $1.80 \times 10^{3}$° C. It is believed that when the first mixture is exposed to a temperature≥$1.20 \times 10^{3}$° C. to produce the second mixture, (i) ≥90.0 wt. % of the first mixture's mercaptans (based on the weight of the first mixture) is converted to hydrocarbon and hydrogen sulfide and (ii) ≤1.0 wt. % of the second mixture's hydrogen sulfide (based on the weight of the second mixture's hydrogen sulfide) combines with the second mixture's $C_2$ unsaturates to produce reversion mercaptans provided the second mixture is exposed to a temperature≥$1.20 \times 10^{3}$° C. When the second mixture is exposed to a temperature<$1.20 \times 10^{3}$° C., the second mixture's hydrogen sulfide can combine with the second mixture's $C_2$ unsaturates, leading to the formation of reversion mercaptans ($C_{2+}$ mercaptans), the rate of reversion mercaptans formation being primarily dependent on the kinetics of this reaction. Exposing the second mixture to a reduced temperature (e.g., a temperature≤300° C., e.g., ≤200° C., such as ≤100° C.) within or proximate to stage 206 can result in, e.g., ≤10.0 wt. %, e.g., ≤1.0 wt. %, such as ≤0.1 wt. % of the second mixture's hydrogen sulfide, based on the weight of the second mixture's hydrogen sulfide, reacting with the second mixture's olefin (thereby producing reversion mercaptans).

In one or more embodiments, ≥25.0 wt. % (such as ≥50.0 wt. % or ≥75.0 wt. %) of the first mixture achieves a peak pyrolysis gas temperature≥$1.40 \times 10^{3}$° C., e.g., in the range of about $1.50 \times 10^{3}$° C. to about $1.675 \times 10^{3}$° C., based on the weight of the first mixture. In an embodiment where it is desired to catalytically convert at least a portion of the second mixture's acetylene to ethylene, the catalyst can be, e.g., a conventional acetylene conversion catalyst, including those having an increased selectivity to ethylene in the presence of carbon monoxide. When such a catalyst is used, an oxygenate such as carbon monoxide can be added to the first mixture, provided the amount of $CO_x$ (x≥1.0) in the second mixture is 20.0 wt. % based on the weight of the second mixture. Optionally, the peak pyrolysis gas temperature is regulated to produce the desired amount of carbon monoxide in the second mixture, e.g., into a range that optimizes the selectivity of the acetylene conversion catalyst utilized in stage 210, e.g., a carbon monoxide: acetylene molar ratio in the range of $3.5 \times 10^{-3}$ to 0.20, such as 0.005 to 0.050. Stage 206 can operate at a total pressure≥10.0 mbar (absolute), e.g., in the range of 0.10 bar to 20.0 bar, such as 1.0 bar to 20.0 bar, or 2.0 bar to 7.0 bar.

Although the process is robust and can operate within a wide range of thermal pyrolysis conditions, e.g., temperature, pressure, residence times, severity, etc., the conditions are generally selected to increase the relative amount of $C_2$ unsaturates in the second mixture, e.g., to increase the acetylene to $C_{3+}$ weight ratio. Relatively long residence times can result in over-cracking of the feed molecules, leading to an undesirable increase in the amount of methane and/or $C_{3+}$ in the second mixture. Relatively long residence time can also result in the reformation of mercaptans, e.g., by the reaction of hydrogen sulfide and olefin in the second mixture. In an embodiment, residence time is ≤about 0.3 seconds, e.g., ≤0.05 seconds. In an embodiment, the pyrolysis is high-severity, thermal pyrolysis and the residence time is ≤0.05 seconds, such as ≤0.02 seconds. Residence time can be selected, e.g., for optimum $C_2$ unsaturates yield under thermal pyrolysis conditions and also, in a regenerative reactor, for preventing the formation of mercaptans in the second mixture by the reaction of unsaturates and hydrogen sulfide. In embodiments where the reactor's temperature exhibits significant variation over the reaction region, as is generally the case in a regenerative, reactor, utilizing a residence time≤about 0.3 seconds, e.g., ≤0.05 seconds, such as ≤0.02 seconds (particularly under high severity conditions) generally result in, e.g., ≤10.0 wt. %, e.g., ≤1.0 wt. %, such as ≤0.1 wt. % of the second mixture's hydrogen sulfide, based on the weight of the second mixture's hydrogen sulfide, reacting with the second mixture's olefin (thereby producing reversion mercaptans). In embodiments where operating at a residence time of ≤about 0.3 seconds does not result in the desired amount of reversion mercaptans, an optional quench of the second mixture can be utilized within or proximate to stage 206 to inhibit their formation.

The $C_2$ unsaturates yield can be optimized by measuring the amount of $C_2$ unsaturates in the second mixture under substantially constant thermal pyrolysis conditions at a plurality of residence times. The optimum residence time can be approximated using conventional interpolation and extrapolation of the measured values. The optimum residence time can also be approximated using pyrolysis reaction simulations of second mixture composition as a function of pyrolysis conditions and residence time, including conventional pyrolysis reaction simulations. The second mixture will now be described in more detail.

III. The Second Mixture

When the specified first mixture is exposed to a temperature≥$1.20×10^3$° C. under pyrolysis conditions, the second mixture comprises ≥1.0 wt. % $C_2$ unsaturates, ≤20.0 wt. % $CO_x$ wherein x≥1.0, and ≤1.0 ppmw thiophene based on the weight of the second mixture. When the first mixture's mercaptans is converted by the pyrolysis into hydrogen sulfide, the second mixture further comprises at least a portion of this hydrogen sulfide. The $C_2$ unsaturates of the second mixture can comprise, e.g., ≥1.0 wt. % acetylene and/or ≥1.0 wt. % ethylene based on the weight of the second mixture. For example, the second mixture can comprise ≥1.0 wt. %, methane, e.g., 2.0 wt. % to 50.0 wt. %; ≥1.0 wt. % molecular hydrogen, e.g., 2.0 wt. % to 50.0 wt. %; ≥1.0 wt. % acetylene, e.g., 2.0 wt. % to 40.0 wt. %; ≥1.0 wt. % ethylene, e.g., 2.0 wt. % to 70.0 wt. %, such as 2.0 wt. % to 20.0 wt. %; and ≥1.0 wt. % $C_{3+}$, e.g., 2.0 wt. % to 50.0 wt. %. The second mixture can further comprise ≥1.0 ppmw hydrogen sulfide, e.g., in the range of $1.0×10^2$ ppmw to $1.0×10^5$ ppmw, such as in the range of $5.0×10^2$ ppmw to $5.0×10^4$ ppmw; ≤10.0 wt. % $CO_x$ wherein x≥1.0; and ≤0.1 ppmw thiophene, the weight percents being based on the weight of the second mixture. Optionally, the second mixture further comprises $C_{3+}$ hydrocarbon, including $C_{3+}$ hydrocarbon which might remain within the pyrolysis region, the amount of $C_{3+}$ hydrocarbon can be, e.g., ≥1.0 wt. % based on the weight of the second mixture, e.g., in the range of 1.0 wt. % to 50.0 wt. %, the weight percents being based on the weight of the second mixture. The second mixture generally comprises ≤0.05 ppmw of methyl mercaptan, e.g., ≤0.01 ppmw, based on the weight of the second mixture, even when the first mixture comprises ≥10.0 ppmw of methyl mercaptan based on the weight of the first mixture. In embodiments where the first mixture comprises diluents (e.g., $N_2$, $H_2O$), such diluents may be present in the second mixture.

Optionally, the second mixture has one or more of the following additional properties: an acetylene:ethylene molar ratio in the range of about 0.5 to about 20.0, e.g., about 1.20 to about 10.0, such as about 2.0 to about 10.0; a molecular hydrogen:$C_2$ unsaturates molar ratio in the range of 2.0 to 20.0; a molecular hydrogen:acetylene molar ratio≥0.75 or ≥3.0, e.g., in the range of 3.0 to 20.0; a molecular hydrogen: ethylene molar ratio≥1.0, e.g., in the range of 1.0 to 100.0; a carbon monoxide: acetylene molar ratio in the range of $3.5×10^{-3}$ to 0.20, such as 0.005 to 0.050; or a carbon dioxide:$C_2$ unsaturates molar ratio≤0.30. In an embodiment, the second mixture has a carbon monoxide:acetylene molar ratio in the range of 0.0035 to 0.20 and comprises $2.0×10^2$ ppmm to $1.0×10^4$ ppmm of carbon monoxide per mole of the second mixture. In embodiments, e.g., where the second mixture is derived from the first mixture under substantially isothermal conditions, the second mixture can have an acetylene:ethylene molar ratio≥about 5.0, e.g., ≥about 10.0, such as ≥about 20.0. Optionally, the second mixture comprises ≤1.0 ppmw mercaptans, and optionally has a mercaptans to hydrogen sulfide weight ratio<0.80, e.g., ≤0.10, such as ≤0.010. Optionally, the second mixture comprises ≤50.0 wt. % water, e.g., ≤10.0 wt. % water, such as ≤1.0 wt. % water; ≤20.0 wt. % $CO_N$, e.g., ≤10.0 $CO_N$, such as ≤2.0 wt. % $CO_x$ wherein x≥1.0; and ≤1.0 ppmw methyl mercaptan based on the weight of the second mixture.

A third mixture derived from the second mixture by the separations occurring, e.g., in stages 206 and/or 208, can be conducted away from stage 208. The third mixture can comprise, consist essentially of, or even consist of that portion of the second mixture which is in the vapor phase at the downstream end of the pyrolysis of stage 206. Such an embodiment can be used, for example, when the third mixture's acetylene is converted to ethylene using a hydrogen sulfide-tolerant acetylene conversion catalyst. Since a significant amount (e.g., substantially all) of the first mixture's mercaptans can be converted to hydrogen sulfide in the thermal pyrolysis, this embodiment is a considerable improvement over conventional acetylene conversion which may utilize a catalyst that is relatively tolerant of hydrogen sulfide but which is mercaptans-intolerant. In conventional cases, catalyst deactivation is prevented by removing mercaptans and mercaptan-forming molecules upstream and/or downstream of the pyrolysis, instead of by converting the first-mixture's sulfur-containing species to hydrogen sulfide (and, potentially, sulfur-containing $C_{3+}$ molecules which remain in the reactor after pyrolysis, and, consequently, requires no additional separation step) as in this aspect of the invention.

The third mixture can be derived from the second mixture in optional upgrading stage 208. For example, stage 208 can include, e.g., means for removing from the second mixture one or more of hydrogen sulfide, diluent, non-volatiles, and molecular hydrogen, hydrocarbon (such as saturated hydrocarbon and/or those containing one or more heteroatoms), etc. For example, stage 208 can include one or more of a tar and/or solid removal means, compression means, adsorption means, distillation means, washing means, or drying means. The invention is advantageous in that mercaptans removal is generally not required in stage 208, the mercaptans of the first mixture being substantially converted to hydrogen sulfide during the thermal pyrolysis of stage 206. Although stage 208 can encompass conventional processing, e.g., conventional separation means, such as those described in U.S. Pat. No. 7,943,808, the invention is not limited thereto.

Separation means can be used, e.g., for removing from the second mixture one or more of condensable species (e.g., condensable hydrocarbon).

In an embodiment, the third mixture is conducted to optional stage 210 for conversion of at least a portion of the third mixture's acetylene, e.g., by one or more of hydrogenation, hydroformylation, cyclicization, alkylation, etc. to produce a first product comprising one or more of ethylene, ethylene glycol, acetic acid, acrylic acid, benzene, toluene, or xylene, styrene, propanol, propanal, or butadiene. In the case of acetylene hydrogenation, the hydrogenation can be "back-end" acetylene conversion, e.g., the acetylene conversion occurs downstream of optional stage 208, the invention is not limited thereto. This description is not meant to foreclose other embodiments, such as those utilizing "front-end" acetylene conversion, e.g., where acetylene conversion is conducted upstream of optional stage 208, those utilizing both front-end and back-end acetylene converters, and those that do not include optional stage 208.

Figure 2A:
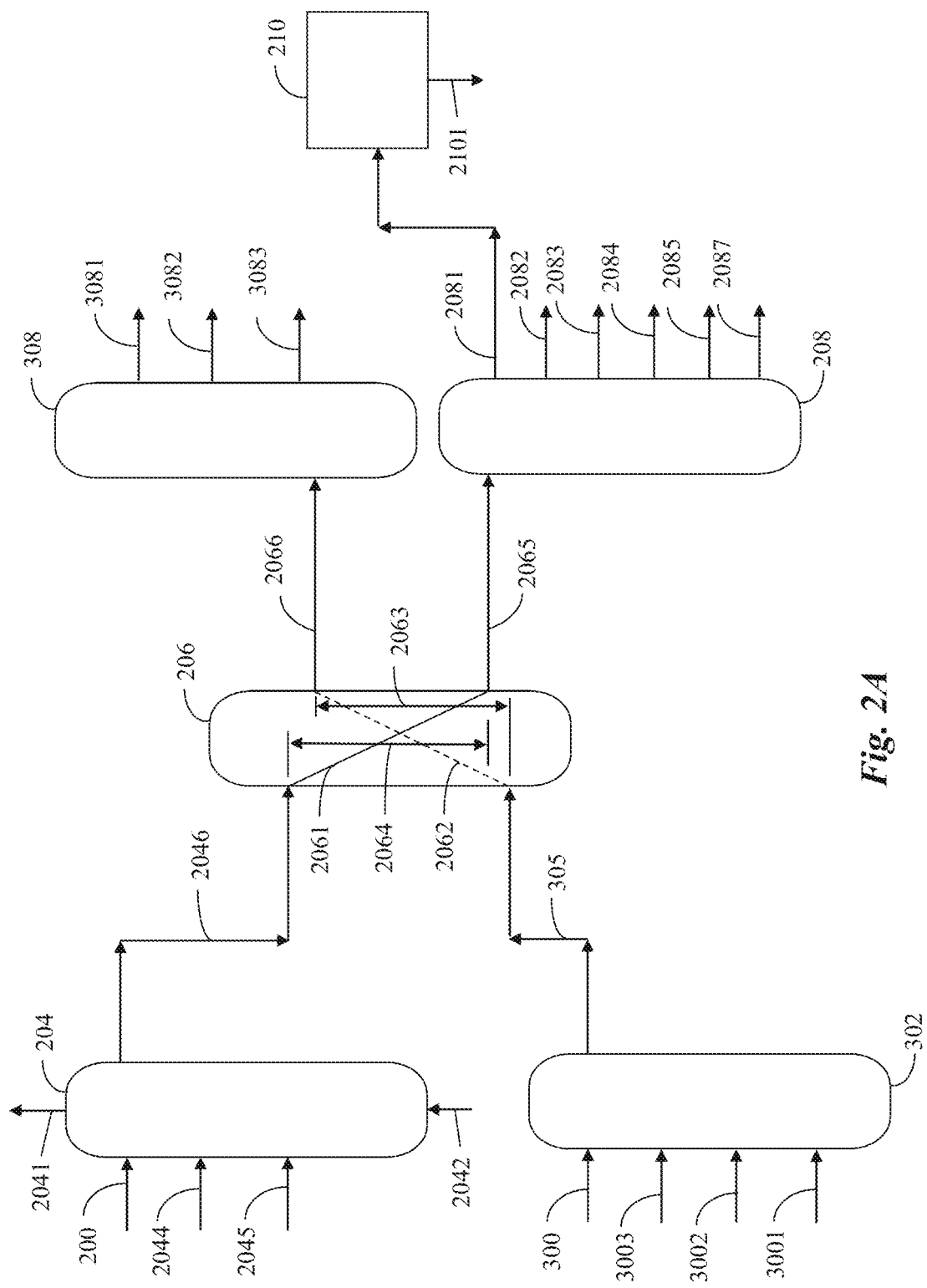
FIG. 2A schematically illustrates an embodiment of the invention utilizing a reverse-flow pyrolysis reactor.

When the acetylene conversion of stage 210 occurs downstream of upgrading/separation stage 208 (e.g., when back-end acetylene conversion is utilized as illustrated in FIG. 2A), stage 208 can include, e.g., means for cooling and then compressing the second mixture conducted away from stage 206 in order to produce the third mixture. For example, in embodiments where stage 206 has an outlet pressure<the inlet pressure of the converter of stage 210, stage 208 can include, e.g., compressing at least the portion of the second mixture from which the third mixture is derived in order to achieve the desired stage 210 inlet pressure. Hydrogen sulfide can be removed from the second mixture downstream of the compression—a desirable location since the gas volume has been reduced significantly during compression. Conventional methods are suitable for removing hydrogen sulfide and other acid gases, e.g., caustic treatment, but the invention is not limited thereto. Acid gases separated from the second mixture can be conducted away, e.g., for storage or further processing such as in a Claus plant. Optionally, a portion of the products of the acetylene conversion of stage 210 is recycled and mixed into the third mixture in stage 208 to further adjust the composition of the third mixture.

If desired, at least a portion of the molecular hydrogen, saturated hydrocarbon, diluent, etc., separated from $C_2$ unsaturates in upgrading stage 208 can be recycled, e.g., by combining such separated species with one or more of the first mixture's source materials, e.g., in preparation stage 204.

When the third mixture is derived from the second mixture by separation, the third mixture can comprise an amount of hydrogen sulfide that is ≤the amount of hydrogen sulfide (on a weight basis) in the second mixture, and further comprises $A_1$ wt. % of saturated hydrocarbon, $A_2$ wt. % of acetylene, and $A_3$ wt. % of ethylene based on the weight of the third mixture. The third mixture can comprise, e.g., ≤1.0×10$^4$ ppmw hydrogen sulfide. Optionally, the third mixture has a molecular hydrogen:acetylene molar ratio in the range of 1.0 to 20.0, the third mixture comprising ≥2.0 wt. % $C_2$ unsaturates based on the weight of the third mixture.

Optionally, the third mixture comprises ≥0.5 wt. % of molecular hydrogen, e.g., 1.0 wt. %, such as in the range of about 1.0 wt. % to about 10.0 wt. % based on the weight of the third mixture. Optionally, $A_1$ is ≥0.0 wt. %, e.g., in the range of from about 0.0 wt. % to about 60.0 wt. %, such as 10.0 wt. % to 50.0 wt. % based on the weight of the third mixture; $A_2$ is ≥0.5 wt. %, e.g., in the range of from about 1.0 wt. % to about 15.0 wt. %, such as 1.0 wt. % to 10.0 wt. % based on the weight of the third mixture; and $A_3$ is ≥25.0 wt. %, e.g., in the range of from about 25.0 wt. % to about 99.0 wt. %, e.g., 40.0 wt. % to 89.0 wt. % based on the weight of the third mixture. The balance of the third mixture (to equal 100.0 wt. %) can further comprise, e.g., molecular hydrogen and/or diluent.

Optionally, the third mixture is substantially free of combustible non-volatiles, e.g., tar, soot, etc. For example, the third mixture can comprise combustible non-volatiles in an amount≤0.10 wt. %, e.g., ≤0.001 wt. %, based on the weight of the third mixture. Optionally, the third mixture has one or more of the following additional properties: an acetylene:ethylene molar ratio≤50.0, e.g., in the range of about 0.01 to about 5.0, such as in the range of about 0.05 to about 1.0; a molecular hydrogen:acetylene molar ratio≥1.0, e.g., in the range of 1.2 to 20.0.

Stage 210 can be utilized for converting at least a portion of the third mixture's acetylene to a first product comprising olefin. Stage 210 will now be described in more detail. The invention is not limited to processes which convert the third mixture's acetylene to olefin, and the following description is not meant to foreclose other conversion processes within the broader scope of the invention.

IV. Optional Process for Deriving the First Product

In stage 210, at least a portion of the third mixture's acetylene is converted to ethylene. For example, stage 210 can include hydroprocessing wherein at least a portion of the hydrogen and $C_2$ unsaturates (particularly acetylene) in the third mixture are converted to a first product having an amount of ethylene (weight basis)≥the amount of ethylene in the third mixture (weight basis). When the amount of hydrogen present in the third mixture is not sufficient for converting the acetylene therein to ethylene, stage 208 can further comprise means for increasing the second mixture's hydrogen content, e.g., by adding hydrogen from a source external to the process, in order to derive a third mixture having the desired amount of hydrogen.

Conventional acetylene conversion catalysts can be used in the catalyst bed(s) of stage 210, but the invention is not limited thereto. For example, suitable catalysts include those comprising one or more elements from Groups Ia and/or VIII of the Periodic Table, e.g., platinum, silver, and/or palladium. Optionally, the catalyst further comprises a support, e.g., a support comprising an inorganic oxide composition such as alumina, silica, or silica-alumina. Optionally, the catalyst has one or more of a bulk density in the range of 0.16 g/cm3 to 1.60 g/cm3 (10.0 pounds per cubic foot to 100.0 pounds per cubic foot), a loss on ignition at 538° C. (1000° F.) of ≤10.0 wt. % based on the weight of the catalyst, a crush strength≥22 Newtons (5.0 pounds), a surface area≥0.1 m2/gram, a particle size (largest dimension)≥0.1 mm, and a pore volume≥0.01 cm3/g.

An acetylene converter of stage 210 can be operated at adiabatic or isothermal acetylene conversion conditions, including one or more of a space velocity ("GHSV") in the range of 1.0×10$^2$ to 1.0×10$^5$, a pressure in the range of 1.0 bar to 100.0 bar, and an average bed temperature (start of run) in the range of 50° C. to 125° C. The invention is compatible with front-end and/or back-end acetylene conversion.

Optionally, at least a portion of the first product is polymerized to form a second product comprising, e.g., polyethylene. Conventional polymerization processes can be used, including those utilizing one or more comonomers with the propylene, but the invention is not limited thereto.

The process can utilize a reverse-flow, regenerative pyrolysis reactor system for at least a portion of the pyrolysis of stage 206. An example of such a process within the scope of the invention will now be described in more detail. The following description is not meant to foreclose other embodiments within the broader scope of the invention.

V. Particular Embodiments Utilizing a Reverse-Flow, Regenerative Pyrolysis Reactor In one or more embodiments, the invention relates to a hydrocarbon conversion process comprising exposing a first mixture to a temperature $\geq 1.2 \times 10^{3°}$ C. at a total pressure $\geq 0.10$ bar (absolute) under thermal pyrolysis conditions in a first region of a reverse-flow, regenerative pyrolysis reactor and conducting away from the first region at least a portion of a second mixture, the second mixture being derived from the first mixture. The process for deriving the second mixture from the first mixture is generally endothermic, and can be conducted, e.g., under high-severity thermal pyrolysis conditions which convert $\geq 90.0\%$ of the first mixture's mercaptans, e.g., $\geq 95.0\%$, such as $\geq 99.0\%$ to hydrocarbon and non-thiophenic, non-mercaptan species in the second mixture, such as hydrogen sulfide and to methane. In this embodiment, the first mixture can comprise, e.g., hydrocarbon, hydrogen sulfide; and $\geq 4.0$ ppmw mercaptans, e.g., $\geq 10.0$ ppmw, such as $\geq 50.0$ ppmw based on the weight of the first mixture, and the second mixture can comprise $\geq 1.0$ ppmw hydrogen sulfide, $\geq 1.0$ wt. % $C_2$ unsaturates, $\leq 20.0$ wt. % $CO_x$ wherein $x \geq 1.0$, and $\leq 1.0$ ppmw thiophene based on the weight of the second mixture. The amount of hydrogen sulfide in the second mixture can exceed the amount of hydrogen sulfide in the first mixture (on a weight basis), because the second mixture can contain (i) that portion of the first mixture's hydrogen sulfide that is not converted by the pyrolysis and (ii) hydrogen sulfide derived from the first mixture's mercaptans during the pyrolysis. Optionally, the second mixture comprises $\geq 0.5$ ppmw, e.g., $\geq 1.0$ ppmw, such as $\geq 5.0$ ppmw more hydrogen sulfide than the first mixture.

Optionally, the process further comprises exothermically reacting at least a portion of first and second reactants of a fourth mixture in a second region of the reverse-flow, regenerative pyrolysis reactor to produce a fifth mixture. The exothermic reacting of the fourth mixture's first and second reactants provides at least a portion of the heat utilized in the first region for deriving the second mixture from the first mixture. The first and second regions can be at least partially coextensive, for example, and the exothermic reacting of the fourth mixture's reactants can be conducted at a substantially different time than the pyrolysis.

In the illustrative embodiments shown in FIG. 2A, stage 206 comprises a reverse-flow, regenerative pyrolysis reactor. In accordance with this embodiment, the first mixture is conducted to a first region 2064 of the reverse-flow, regenerative pyrolysis reactor via at least one conduit 2046. The first and second reactants of the fourth mixture are conducted to a second region 2063 of the reactor via conduit 305. The first and second reactants are conducted to region 2063 through separate channels within conduit 305, the first and second reactants being combined to produce the fourth mixture (for the exothermic reaction) in proximity to the downstream end of conduit 305 and the upstream end of region 2063. In another embodiment, the first reactant is conducted to region 2063 via conduit 305, with the second reactant being conducted to region 2063 via a second conduit (3051—not shown).

The first and second regions are at least partially coextensive as shown. The first mixture is derived from one or more source materials 200, e.g., natural gas, etc. Optionally, one or more of the source materials are upgraded in optional preparation stage 204 to produce the first mixture. The fourth mixture comprises first and second reactants. The first reactant can be, e.g., fuel, and the second reactant can be, e.g., oxidant. The fuel can be derived from at least one second source material 300, e.g., natural gas, petroleum, other hydrocarbon, etc., including fractions, products, or byproducts thereof. The oxidant can comprise, e.g., oxygen, etc., and can be derived, e.g., from a source material (not shown) such as air. Optionally, one or more of the fourth mixture's source materials is upgraded in a second preparation stage 302 upstream of conduit 305 and optional conduit 3051 (not shown). Stage 302 can optionally include one or more of separation, conversion, addition of recycled portions of the second and/or fifth mixtures, etc. In this embodiment, the reactor 206 is (i) "reverse flow" in the sense that the upstream region of the reactor with respect to the first mixture is the downstream region with respect to the fourth mixture and (ii) "regenerative" in the sense that at least a portion of the heat consumed during the conversion of the first mixture is provided by oxidizing the fourth mixture.

Continuing with the illustrative embodiments of FIG. 2A, fuel is conducted via a first channel (or plurality thereof) in conduit 305 and oxidant is conducted via a second channel (or plurality thereof) in conduit 305 or optionally via a second conduit 3051 (not shown) to the second region 2063. Although the invention is described in terms of a fourth mixture comprising fuel and oxidant, the invention is not limited thereto, and this description is not meant to foreclose other first and second reactants within the broader scope of the invention. Optionally at least a portion of conduit 305 (and/or conduit 3051 when utilized) is located within the reactor of stage 206.

Proximate to the downstream end of conduits 305 (or 305 and 3051), the fuel and oxidant are combined to produce the fourth mixture, the fuel and oxidant then reacting exothermically in the second region 2063 (the flow of the first and second reactants and the products thereof being represented by dashed line 2062). The exothermic reaction provides at least a portion of the heat utilized in the coextensive portion of region 2064 during the pyrolysis. The fifth mixture, comprising at least a portion of the compositions resulting from the reaction of the fourth mixture's fuel and oxidant (and optionally including (i) a portion of the fourth mixture that is not consumed in the reaction and/or (ii) products of the combustion of combustible non-volatiles present in stage 206 from pyrolysis), is conducted away from stage 206 via a conduit 2066. Optionally, at least a portion of conduit 2066 is located within the reactor of stage 206.

After at least a portion of the fourth mixture's fuel and oxidant are exothermically reacted in region 2063 (e.g., by an oxidation reaction such as combustion), the first mixture is conducted to the upstream end of region 2064 via conduit 2046. Optionally, at least a portion of conduit 2046 is located within the reactor of stage 206. The first mixture traverses region 2064 (the traversal being represented by solid line 2061), abstracting heat from region 2064 and thereby deriving the second mixture. In this embodiment, at least a portion of the heat abstracted by the first mixture in region 2064 is produced in region 2063 by the reaction of the first and second reactants. Optionally, a major amount (e.g., >50.0%) of the heat abstraction occurs in the portion of region 2064 that is coextensive with region 2063. The second mixture is conducted away from stage 206 via at least one conduit 2065. Optionally at least a portion of conduit 2065 is located within the reactor of stage 206. In an embodiment, conduit 2065 comprises at least a portion of the channels within conduit 305; which can serve, e.g., to preheat the fuel and/or oxidant of the fourth mixture before combustion Optionally, after at least a portion of the second mixture is conducted away from region 2064, the fuel and oxidant utilized to produce the fourth mixture are again conducted through separate channels within conduit 305 to region 2063, and the process repeats in sequence—exothermically reacting the fuel and oxidant of the fourth mixture to heat the reactor and then utilizing at least a portion of the heat for pyrolysing the first mixture. The process can thus be operated sequentially, e.g., continuously, semi-continuously, or even in batch mode. In an embodiment, stage 206 comprises a plurality of pyrolysis reactors operating, e.g., in series, parallel, or a combination thereof Continuing with the illustrative embodiments of FIG. 2A, the first product is conducted away from conversion stage 210 via a conduit 2101, e.g., for polymerizing at least a portion of the first product's unsaturates.

Optionally, these embodiments further include one or more of the following components: a second upgrading stage 308 for upgrading the fifth mixture downstream of conduit 2066; one or more conduits for adding to the fourth mixture's fuel source materials one or more of light saturated hydrocarbon such as methane 3001 or diluent (such as oxygenate) 3002; conduits for adding to the fourth mixture's oxidant source material(s) additional or supplemental oxidant 3003; one or more conduits for adding to the first mixture's source material one or more of diluent such as; hydrocarbon, e.g., light saturated hydrocarbon such as methane 2044, or oxygenate 2045; conduits for conducting hydrogen 2042 to preparation stage 204 and for conducting away heteroatom species such as hydrogen sulfide or non-volatiles 2041; one or more conduits for conducting away a first byproduct from upgrading stage 308, the first byproduct including at least one of non-oxidized hydrocarbon 3081 and 3082; a conduit 3083 for conducting heteroatom species such as $NO_N$, $SO_x$, $CO_2$, $N_2$, sulfuric acid, etc. away from upgrading stage 308; one or more conduits for conducting a second byproduct away from stage 208, the second byproduct including at least one of molecular hydrogen 2082 or light saturated hydrocarbon 2083; one or more conduits for conducting away non-volatiles 2084, heteroatom species such as hydrogen sulfide 2085, or unsaturated hydrocarbon 2087 away from upgrading stage 208; or one or more conduits (not shown) for adding to the second mixture one or more of (i) hydrogen; (ii) methane, ethane, and/or other light saturated hydrocarbon; or (iii) ethylene. In an embodiment, (a) the first, second, and third mixtures are substantially the same as those described in sections I and III and (b) stages 204, 206, 208, and 210 operate substantially the same way as described in sections II-V. The fourth and fifth mixtures will now be described in more detail.

VI. Fourth and Fifth Mixtures

Exothermically reacting first and second reactants can provide at least a portion of the heat utilized by the pyrolysis. For example, the first and second reactants can be mixed within a pyrolysis reactor to produce a fourth mixture, the first and second reactants then reacting, e.g., by an oxidation reaction such as combustion, as the fourth mixture traverses at least a portion of the pyrolysis reactor. In another embodiment, the first and second reactants are combined upstream of the pyrolysis reactor, with at least a portion of the first and second reactants exothermically reacting within the pyrolysis reactor. The first reactant can comprise, e.g., molecular hydrogen, synthesis gas (mixtures of carbon monoxide and molecular hydrogen), or hydrocarbon, such as $\geq 10.0$ wt. % hydrocarbon (including mixtures thereof), or 50.0 wt. % hydrocarbon, or 90.0 wt. % hydrocarbon based on the weight of the first reactant. The second reactant can comprise, e.g., $\geq 10.0$ oxidant, e.g., or 50.0 wt. % oxidant, or 90.0 wt. % oxidant based on the weight of the second reactant. Optionally, the fourth mixture further comprises diluent. When the first reactant comprises hydrocarbon, the particular hydrocarbon selected is not critical. For example, in an embodiment, the hydrocarbon comprises one or more of the hydrocarbons specified for the first mixture, e.g., methane. When the first reactant comprises hydrogen and/or hydrocarbon and the second reactant comprises oxidant, the choice of oxidant is not critical, provided the oxidant is capable of exothermically reacting with the hydrogen and/or hydrocarbon. For example, in an embodiment, the oxidant comprises, e.g., molecular oxygen.

Referring to FIG. 2A, in cases where the fuel source material(s) 300 are too lean in one or more of hydrocarbon (e.g., light hydrocarbon such as methane), hydrogen, or diluent, these can be added through conduit 3001. When the source material does not contain sufficient oxidant, it can be added to stage 302 via one or more conduits 3003. For example, in some embodiments it is beneficial to increase the amount of oxidant in the fourth mixture beyond that needed to oxidize substantially all of the fourth mixture's fuel, e.g., in embodiments where the pyrolysis of the first mixture deposits a hydrocarbon-containing residue in the pyrolysis reactor and the process would benefit from oxidizing at least a portion of the residue. In other embodiments, it is beneficial to lessen the amount of oxidant in the fourth mixture, e.g., when it is desired to conduct the oxidizing of the fourth mixture under partial oxidation conditions. In still other embodiments, it is beneficial for the fourth mixture to contain a substantially stoichiometric amount of oxidant, i.e., the amount of oxidant needed to oxidize substantially all of the fourth mixture's fuel.

Optionally, the fourth mixture further comprises diluent, e.g., $\geq 1.0$ wt. % of diluent based on the weight of the first mixture. The fourth mixture can include diluents (which can be a diluent mixture) such as one or more of, e.g., oxygenate such as water and/or carbon dioxide, non-combustible species, nitrogen ($N_2$), or inert gas (including inert gas mixtures). When the diluent comprises a portion of compositions recycled from the second or fifth mixture, the diluent may comprise one or more of amines, mixtures of amines, non-volatiles (whether combustible or not) including refractory inorganics, etc. In an embodiment, the fourth mixture comprises $\leq 96.0$ wt. % diluent, e.g., in the range of 65.0 wt. % to 94.5 wt. % diluent, based on the weight of the fourth mixture.

The fourth mixture generally comprises $\geq 1.0$ wt. % molecular oxygen, e.g., in the range of 5.0 wt. % to 25.0 wt. %, such as 7.0 wt. % to 15.0 wt. %; $\geq 0.1$ wt. % fuel, e.g., in the range of 0.5 wt. % to 10.0 wt. %, such as 1.0 wt. % to 5.0 wt. %, the weight percents being based on the weight of the fourth mixture, with the balance of the fourth mixture being diluent.

The fifth mixture comprises (i) products derived from the exothermic reaction of the fourth mixture's first and second reactants, (ii) products derived from oxidizing combustible non-volatiles deposited in stage 206 during pyrolysis, (iii)

diluent, when diluent is present in the fourth mixture, and optionally (iv) unreacted first and/or second reactants. When the exothermic reaction of the first and second reactants involves hydrocarbon combustion, or when a diluent is present in the fourth mixture (such as $N_2$ or $H_2S$), the fifth mixture can comprise carbon dioxide, and can further comprise sulfur oxides, nitrogen oxides, etc. Since the first mixture's mercaptans is generally converted to sulfur compounds that are in the vapor-phase portion of the second mixture, the fifth mixture generally comprises ≤10.0 ppmw, $SO_y$ (y≥2.0, e.g., in the range of from 2 to 4) based on the weight of the fifth mixture.

A continuous or semi-continuous process for deriving (a) the second mixture from the first mixture and (b) the fifth mixture from the fourth mixture will now be described in more detail. Although the process is described in terms of a reverse-flow, regenerative pyrolysis reactor, the invention is not limited thereto, and this description is not meant to foreclose other embodiments within the broader scope of the invention.

VII. Continuous or Semi-Continuous Process

Referring to FIG. 2A, the first reactant is conducted via one or more first channels within conduit 305 and the second reactant is conducted via one or more second channels within conduit 305 or optionally via a second conduit 3051 (not shown). The first and second reactants are thus conducted separately to the upstream end of region 2063, where the first and second reactants are combined to form the fourth mixture. A fifth mixture, derived from the exothermic reacting of at least a portion of the fourth mixture's first and second reactants in region 2063 is conducted away from stage 206 via conduit 2066. In an embodiment, the first reactant is fuel and the second reactant is oxidant, the reacting including a combustion or partial combustion of at least a portion of the fuel utilizing at least a portion of the oxidant. At least a portion of the heat of combustion is utilized to increase the temperature of region 2064. At the conclusion of the combustion step, the fifth mixture is conducted away via conduit 2066 and the first mixture is introduced into the reactor (optionally after an optional purge of the fifth mixture from stage 206 by a non-reacting material such as an inert purge gas). The relative types and amounts of the first and second reactants are selected so that the (exothermic) heat of reaction obtained during the reaction sufficiently heats region 2064, particularly the portion of region 2064 that is coextensive with region 2063, for exposing the first mixture to a temperature≥$1.40\times10^{3\circ}$ C.

Pyrolysis reactor of stage 206 can be, e.g., one or more of the pyrolysis reactors described in U.S. Pat. No. 7,943,808. For example, the reactors of that reference provide a high-temperature heat bubble formed in the middle of a packed-bed reactor system. The reactor system can be utilized in a two-step process wherein heat is (1) added to the bed via in-situ combustion (e.g., of the fourth mixture) and then (2) removed from the bed via pyrolysis (e.g., in-situ endothermic reforming of the first mixture). For example, in one embodiment the reactor system comprises two reactors: (a) a first (heat recuperating) reactor and (b) a second (pyrolysis) reactor. Deriving the second mixture from the first mixture in such a system does not require a catalyst, though one can be used, e.g., to optionally convert light hydrocarbon (e.g., methane) in the first mixture to acetylene.

The reactor system can operate, e.g., in series, parallel, or a combination thereof, and utilizes accompanying valve means for conducting the first, second, fourth, and fifth mixtures to/from the reactors of the reactor system. For example, in one embodiment the reactor system includes first and second reactors, oriented in a series relationship with each other with respect to a common flow path, optionally along a common axis. The common axis may be horizontal, vertical, or some other orientation with respect to the surface of the earth.

Conduits 305 and 3051 (or one or more segments thereof) can be in the form of separate but substantially parallel passages located within a quenching reactor bed (e.g., the first reactor), the first reactor being located within stage 206. In other words, in this embodiment the first and second reactants are conducted toward the second reactor via substantially independent flow paths (e.g., the first reactor can be a ceramic article with channels located therein). Optionally, the first and/or second reactants abstract heat from the first reactor. Optionally, other components utilized to produce the fourth mixture, e.g., diluent, can be conducted through the first reactor together with the first reactant, the second reactant, or a portion with each. When the components utilized to produce the fourth mixture (optionally heated by the hot first reactor) reach a designated location within the reactor system, the components are combined and at least a portion of the fourth mixture's first reactant exothermically reacts with at least a portion of the fourth mixture's second reactant in region 2063.

The exothermic reaction can include an oxidization (e.g., combustion) of the first reactant, the first reactant being, e.g., hydrogen and/or hydrocarbon. Such a combustion can result in a high temperature zone (also referred to by those skilled in the art as a temperature bubble), at least a portion of the temperature bubble being located in region 2063 and having a temperature≥$1.50\times10^{3\circ}$ C., e.g., in the range of about $1.60\times10^{3\circ}$ C. to about $1.70\times10^{3\circ}$ C. Optionally, the combustion completely oxidizes the oxidizable species (e.g., fuel) in the first reactant, including hydrocarbon, hydrogen, etc., therein. Optionally, ≥50.0% of the combustion (based on the amount of the fourth mixture, mole basis, that is oxidized in region 2063), e.g., ≥75.0%, such as ≥90.0% of the combustion occurs in the portion of region 2063 that is located between the first and second reactors. Optionally, the combustion duration is for a time sufficient for (i) the second reactor to abstract heat from the combustion, the second reactor being located at least partially within zone 2063 but downstream of the first reactor with respect to the flow of the fourth mixture and/or (ii) to oxidize ≥90.0 wt. % of combustible non-volatiles in stage 206, the weight percent being based on the weight of combustible non-volatiles present in stage 206 at the start of the oxidation. In other words, the combustion optionally displaces the temperature bubble, into and at least partially through the second reactor. For efficiency, it is generally undesirable to displace the heat bubble past the downstream end (with respect to the flow of the fourth and fifth mixtures) of the second reactor, e.g., to avoid waste of heat and/or overheating the second reactor. In an embodiment, the fifth mixture, derived from the combustion of the fourth mixture, is conducted through the second reactor and away from stage 206.

Optionally, the total amount of heat added to the reactor system during the exothermic reaction of the first and second reactants (e.g., the regeneration step) does not exceed the sum of the heats that are required (a) to sustain the pyrolysis reaction for endothermically driving the second mixture from the pyrolysis portion of the first mixture and (b) for heat losses from the system, e.g., by as conduction losses through reactor walls and/or convective losses with, e.g., the second mixture. Optionally, the total amount of heat stored in the reactor system though is generally much more than the minimum amount of heat needed for the pyrolysis in any single cycle of a continuous or semi-continuous process.

After at least a portion of the fourth mixture's hydrocarbon has been oxidized, the pyrolysis portion of the first mixture is conducted to the upstream end of region 2064, e.g., the upstream end of the second reactor, where upstream is now defined with respect to the flow of the first and second mixtures. Optionally, a reactor purge, e.g., an inert gas sweep, can be used between the oxidation and pyrolysis steps. Optionally, the first mixture is exposed to a temperature $\geq 1.50 \times 10^{3\circ}$ C. under high severity thermal pyrolysis conditions, e.g., in the portion of region 2064 that is coextensive with region 2063 via proximity to the second reactor and other reactor internals (e.g., mixer media) located, e.g., in the temperature bubble region, which have been heated by the exothermic reaction of the first and second reactants. Optionally, at least a portion of the temperature bubble region is located within the portion of zone 2064 that is coextensive with zone 2063.

Stage 206 can include a reactor system shown schematically in FIGS. 3a and 3b. Referring now to FIG. 3, the reactor system comprises two reactors: a first (recuperator/quenching) reactor 7 and a second (pyrolysis) reactor 1. Optionally, the first and second reactors both contain regenerative beds, where the term "regenerative bed" means a reactor bed comprising materials that are effective in storing and transferring heat, and optionally useful for carrying out a chemical reaction. In an embodiment, the regenerative beds comprise bedding or packing material such as glass or ceramic beads or spheres, metal beads or spheres, ceramic (including, e.g., alumina, yttria, zirconia, etc., and mixtures thereof) or metal honeycomb materials, ceramic tubes, extruded monoliths, catalysts, etc. Optionally, the materials comprising the regenerative bed maintain integrity, functionality, and withstand long term exposure to temperatures in excess of 1200° C., preferably in excess of 1500° C., more preferably in excess of 1700° C., and even more preferably in excess of 2000° C. for operating margin.

Figure 2B:
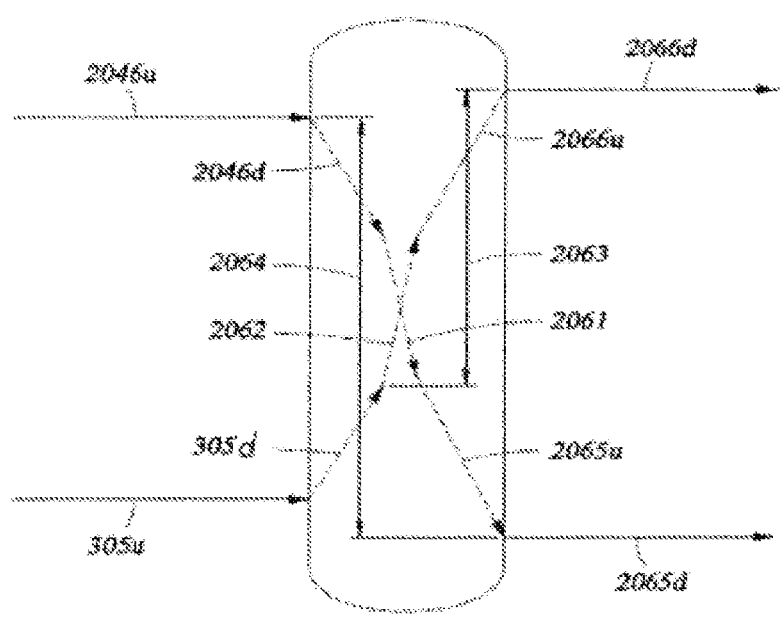
FIG. 2B schematically illustrates one pyrolysis reactor configuration.

The continuous or semi-continuous process can begin with a "pyrolysis" step wherein (a) the downstream end 5 of the second reactor 1 (downstream with respect to the flow of the first mixture, as shown in FIG. 3a) is at a temperature $\geq$ than that of the upstream end 3 and (b) at least a portion (including the downstream end 9) of the first reactor 7 is at a temperature less than that of the downstream end of the second reactor 5 in order to provide a quenching effect for the second mixture. The first mixture is conducted to the upstream end 3 of the second reactor via conduit 2046. Optionally, conduit 2046 comprises upstream 2046u and downstream segments 2046d, as shown in FIG. 2B. Upstream segment 2046u (represented in the figure by a solid line) is external to the second reactor 1. Downstream segment 2046d (represented by a dashed line), is in fluid communication with 2046u and is located within second reactor (1), e.g., as one or more passages within the reactor.

Continuing with reference to FIG. 3a, the first mixture abstracts heat from the first reactor, resulting in the derivation of the second mixture from the first by thermal pyrolysis. As this step proceeds, a shift in the temperature profile 2 occurs (e.g., a shift in the trailing edge of the temperature bubble as indicated by the arrow), the amount of this shift being influenced by, e.g., the heat capacity and heat transfer properties of the system. At least a portion of the second mixture, e.g., the portion in the vapor phase, is conducted from the downstream end 5 of the second reactor to the upstream end 11 of the first reactor 7, and is conducted away from the first reactor via conduit 2065 proximate to the downstream end 9, as shown. Optionally, conduit 2065 comprises upstream 2065u and downstream segments 2065d, as shown in FIG. 2B. Downstream segment 2065d (represented in the figure by a solid line) is external to the first reactor 7. Upstream segment 2065u (represented by a dashed line), is in fluid communication with 2065d and is located within the first reactor 7, e.g., as one or more passages within the reactor. At the start of thermal pyrolysis, the first reactor 7 has a temperature less than that of the second reactor 1. As the second mixture traverses the first reactor 7, the second mixture is quenched (e.g., cooled) to a temperature approaching that of the downstream end 9 of the first reactor. As the second mixture is quenched in the first reactor 7, the leading edge of the temperature bubble 4 moves toward the downstream end 9 of the first reactor 7. In at least one of the embodiments represented by FIG. 3a, the upstream end of pyrolysis region 2064 (referenced in FIGS. 2A and 2B) is proximate to the upstream end 3 of the second reactor 1. The downstream end of pyrolysis region 2064 is proximate to the downstream end 9 of the first reactor 7. Since the quenching heats the first reactor 7, the combustion step optionally includes cooling the first reactor, e.g., to shift the leading edge of the temperature bubble away from end 9 of the first reactor 7, as illustrated schematically in FIG. 3b.

If desired, the pyrolysis step can include one or more of the following conditions: the first mixture achieves a peak pyrolysis gas temperature $\geq 1.40 \times 10^{3\circ}$ C., e.g., in the range of $1.45 \times 10^{3\circ}$ C. to $2.20 \times 10^{3\circ}$ C., such as, $1.50 \times 10^{3\circ}$ C. to $1.90 \times 10^{3\circ}$ C., or $1.60 \times 10^{3\circ}$ C. to $1.70 \times 10^{3\circ}$ C.; a total pressure $\geq 1.0$ bar (absolute), e.g., in the range of 1.0 bar to about 15 bar, such as in the range of 2.0 bar to 10.0 bar; and/or a residence time under high severity conditions of $\leq 0.1$ seconds, e.g., $\leq 5.0 \times 10^{-2}$ seconds, such as $\leq 5.0 \times 10^{-3}$ seconds. When it is desired to increase the amount of one or more of molecular hydrogen, hydrocarbon (e.g., light saturated hydrocarbon such as methane), and diluent in the first mixture, these can be added (e.g., in stage 204) as follows:

(i) Molecular hydrogen can be added via conduit 2042, with the added hydrogen obtained, e.g., from one or more of (a) from the process via conduit 2082 when optional stage 208 is present, (b) from molecular hydrogen separated from the first product, or (c) from an external source.

(ii) Hydrocarbon can be added via conduit 2044. These species can be obtained from the process via conduit 3081 or 2083, e.g., when optional stages 308 and 208 are utilized, from hydrocarbon separated from the first product, or from an external source.

(iii) Diluent can be added via conduit 2045. The diluent can be obtained, e.g., (a) from the process via conduit 3082, when optional stage 308 is utilized separated from the first product, (b) steam, e.g., steam generated in a process cooler, and/or (c) from a source external to the process.

It is understood that flow control means (e.g., one or more of valves, rotating reactor beds, check valves, louvers, flow restrictors, timing systems, etc.) can be used to control gas flow, actuation, timing, and to alternate physical beds between the flow systems for the first, second, fourth, and fifth mixtures, and the optional purge gas when used. The combustion step will now be described in more detail, with reference to FIG. 3b.

The second step of the process, referred to as the combustion or regeneration step, begins by separately conducting first and second reactants to the first reactor 7, with the term "upstream" now being with respect to the flow of the fourth mixture, as shown in FIG. 3b. The first and second reactants are conducted to first reactor 7 via conduit (or a plurality of conduits) 305 and optionally 3051 (not shown). The first reactant can be conducted via first passage(s) located within conduit 305, and the second reactant is separately (and optionally simultaneously) conducted via second passage(s) within conduit 305 or via passage(s) in a second conduit 3051 (not shown). Optionally, conduit 305 comprises upstream 305u and downstream segments 305d, as shown in FIG. 2B. Upstream segment 305u (represented in the figure by a solid line) is external to first reactor 7. Downstream segment 305d (represented by a dashed line), is in fluid communication with 305u and is located within first reactor 7, e.g., as one or more passages therein. When conduit 3051 is utilized to convey the second reactant, conduit 3051 can comprise upstream 3051u and downstream 3051d segments; 3051u and 3051d being in fluid communication, and wherein (a) 3051u is located external to first reactor 7 and (b) 3051d is located within first reactor 7, e.g., as one or more of a second set of passages therein, the first set of passages being those of conduit 305d. Conduits 305 and 3051 can include one or more spargers and/or distributors for conveying the first and second reactants from upstream segments 305u and 3051u into downstream segments 305d and 3051d. Suitable spargers, distributers, and configurations for using these to connect conduit segments are disclosed in U.S. Pat. No. 7,815,873 which is incorporated by reference herein in its entirety. Accordingly, the first and second reactants separately traverse first reactor 7 through their separate passages (in other words the first and second reactants do not mix appreciably in the first reactor) and exit the downstream end 11 of the first reactor 7 where the first and second reactants are combined to produce a fourth mixture. The first and second reactants of the fourth mixture react exothermically at or proximate to a central region 13 of the reactor system. Optionally, the exothermic reaction continues downstream (with respect to the average flow of the fourth mixture) of region 13, e.g., in second reactor 1. Although this embodiment is described in terms of the first and second reactants separately traversing first reactor 7, the invention is not limited thereto, and this description is not meant to foreclose other embodiments within the broader scope of the invention, such as (a) embodiments where the first and second reactants are mixed to produce the fourth mixture, with the fourth mixture traversing reactor 7; or (b) embodiments where the first reactant is conducted into and through first reactor 7 via conduit 305 with the second reactant being conducted to region 13 via conduit 3051 by a path external to first reactor 7. The fifth mixture, comprising any unreacted fourth mixture and products resulting from the reaction of the first and second reactants, is conducted away from second reactor 1 via one or more conduits 2066. Optionally, conduit 2066 comprises upstream 2066u and downstream segments 2066d, as shown in FIG. 2B. Downstream segment 2066d (represented in the figure by a solid line) is external to second reactor 1. Upstream segment 2066u (represented by a dashed line), is in fluid communication with 2066d and is located within the second reactor 1, e.g., as one or more channels within the reactor.

The combustion step thus includes the following features: (i) heating of region 13 and the second reactor 1 by transferring at least a portion of the heat of combustion to the reactor system downstream of the end 11 of the first reactor and (ii) by transferring at least a portion of the sensible heat recovered by the first and second reactants in an upstream region of the first reactor (upstream with respect to the flow of the fourth mixture and components thereof) toward the downstream region of the first reactor, region 13 and/or the second reactor in order to thermally regenerate the reactor system. Accordingly, the trailing edge 8 and leading edge 6 of the temperature bubble translate downstream from their starting locations at the beginning of the combustion step, as shown in FIG. 3b.

In the embodiments of FIG. 3b, the exothermic reaction region 2063 can be located, e.g., between a first point proximate to the downstream end 11 of first reactor 7 and a second point proximate to the downstream end 3 of second reactor 1. Referring to FIG. 3b, the pyrolysis region can be located, e.g., between a first point proximate to the upstream end 3 of the second reactor 1 and a second point proximate to the downstream end 9 of first reactor 7. Referring now to FIG. 2B, it should be appreciated that the invention can be practiced without precisely defining (a) the boundaries of regions 2063 and 2064, (b) the precise locations of the intersections of flow-path 2062 with segments 305d and 2066u, or (c) the precise locations of the intersections of flow-path 2061 with segments 2046d and 2065u (the intersection locations being schematically depicted by inflections). Although region 2063 (the exothermic reaction region) is at least partially coextensive with pyrolysis region 2064, the upstream end of region 2063 is proximate to the location where sufficient first and second reactants have combined to produce an exothermic reaction, this location being indicated in FIG. 2B as an inflection between segment 305d and flow-path 2062. The downstream end of region 2063 is generally proximate to the downstream end of second reactor 1 as shown in FIG. 2B, though this is not required, and in at least one embodiment, the downstream end of region 2063 is located further downstream, e.g., in conduit 2066d. The intersection of flow-path 2062 (which encompasses at least a portion of region 13 and optionally, e.g., at least a portion of reactor 1) with segment 305d (and 3051d) is generally proximate to the downstream end 11 of first reactor 7 (downstream with respect to the average flow of the fourth mixture), since that is where the first and second reactants combine. The practice of the invention does not require precisely defining the intersection of flow-path 2062 and segment 2066u. The practice of the invention does not require precisely defining the intersection of flow path 2061 (which encompasses at least a portion of region 13 and optionally, e.g., portions of reactors 1 and/or 7 and segments 2046d and 2065u). It should be recognized that the oscillatory translation of the leading and trailing edges of the temperature bubble during the combustion and pyrolysis steps confines the temperature bubble (which can achieve temperatures e.g., >1600° C.) to regions of the reactor system that can tolerate such conditions long-term.

At least a portion of the means utilized for conveying the first mixture into and through the first reactor, e.g., at least a segment of conduit 2046d, can also be utilized for conveying at least a portion of the fifth mixture, e.g., as conduit 2066u. In an embodiment, at least a portion of the means utilized for conveying the first and second reactants, e.g., at least a portion of conduit 305d (and/or 3051d), is also utilized for conveying at least a portion of the second mixture, e.g., via conduit 2065u.

Optionally, (a) segment 305d comprises a plurality of first passages (each passage, e.g., comprising an independent flow path) in the first reactor 7 and (b) segment 3051d comprises a plurality of second passages that may have the same or different cross sectional shape and size compared to those of the plurality of first passages. In one embodiment, the first reactor includes the first and second plurality of passages interdigitated in a honeycomb monolith structure.

Honeycomb monoliths include, e.g., extruded porous structures such as those that are used for automotive catalytic converters, etc. The term "honeycomb" means a cross-sectional shape that includes multiple flow paths or passages through the extruded monolith, but the use of this term is not meant to limit the monolith's structure or shape to any particular topology. In embodiments where a honeycomb monolith is used, the honeycomb monolith enables low pressure loss transference while providing contact time and heat transfer. Optionally, a mixer is used between the first and second reactors to improve combustion. Mixer means, distributor means, reactor system internals, valve means, etc., for the reactor system included in stage 206 can be substantially the same as those described in U.S. Pat. No. 7,943,808, for example. Representative combustion conditions will now be described in more detail.

The exothermic reaction of the first and second reactant components of the fourth mixture can include combustion, the combustion conditions including a temperature$\geq 1.40 \times 10^{3\circ}$ C., e.g., $\geq 1.50 \times 10^{3\circ}$ C. such as $\geq 1.60 \times 10^{3\circ}$ C., e.g., in the range of $1.90 \times 10^{3\circ}$ C. to $2.20 \times 10^{3\circ}$ C., and a pressure$\geq 1.0$ bar (absolute), e.g., in the range of 1.0 bar to 15.0 bar, such as 2.0 bar to 5.0 bar. When it is desired to increase the relative amount of (i) one or more of hydrocarbon (e.g., methane) and/or hydrogen in the first reactant over that of the its source material or (ii) increase the relative amount of oxidant (e.g., oxygen and/or ozone) in the second reactant over that of its source material, this can be done as follows: (i) Hydrocarbon, such as light saturated hydrocarbon, e.g., methane, can be added via conduit 3001. These species can be obtained from (i) external sources and/or (ii) sources within the process such as from conduits 3081 or 2083, e.g., when optional stages 308 and 208 are utilized.
(ii) Oxidant can be added via conduit 3003. The added oxidant can be obtained from (i) external sources and/or (ii) sources within the process such as from conduit 3082, e.g., when the diluent in conduit 3082 comprises oxidant. When the source material is air, the air can be obtained from a blower or compressor, for example.

Continuing with reference to FIG. 2A, at the conclusion of the combustion step optional upgrading stage 308 can be used, e.g., to separate from the fifth mixture species that may be useful in other stages of the process, e.g., via conduits 3081-3083 as discussed. The portion of the second mixture that is not used in other stages of the process can be conducted away from the process via one or more conduits 2087 for storage or further processing. At the conclusion of the pyrolysis step, optional upgrading stage 208 can be used, e.g., to separate from the second mixture species that may be useful in other stages of the process, e.g., via conduits 2082. A third mixture is derived from the second mixture, e.g., in stages 208, and is conducted via conduit 2081 to conversion stage 210. In embodiments where downstream stages for, e.g., acetylene conversion, polymerization, etc., operate at a higher pressure than the pyrolysis stage 206, means for increasing the second and/or third mixtures' pressure can be utilized, e.g., in stage 208 and locations downstream thereof. Conventional means for increasing pressure are suitable, e.g., one or more compressors, blowers, etc., though the invention is not limited thereto.

Stages downstream of stage 206, including optional stages, can be operated in the continuous process as specified in the preceding embodiments.

Example 1

The following prophetic example is conducted. A first mixture is exposed to a time averaged (over the duration of the pyrolysis step) peak pyrolysis temperature of $1.625 \times 10^{3\circ}$ C. for a residence time of about $1.0 \times 10^2$ milliseconds at a total pressure of 5.0 bar (absolute) to produce a second mixture; the first mixture comprising 80.0 wt. % of methane, 20.0 wt. % of molecular hydrogen, and 10.0 ppmw of methyl mercaptan based on the weight of the first mixture; and the second mixture comprising 21.1 wt. % of acetylene, 13.8 wt. % of ethylene, 24.0 wt. % of methane, 1.6 wt. % of ethane, 29.4 wt. % of molecular hydrogen, 10.1 wt. % of $C_{3+}$, $\leq 0.1$ ppmw of methyl mercaptan, $\leq 0.1$ ppmw of thiophene, and 8.5 ppmw of hydrogen sulfide based on the weight of the second mixture. Following the pyrolysis the second mixture is exposed to a temperature$\leq 100.0°$ C., which lessens the amount of reversion mercaptans formation from, e.g., the reaction of the second mixture's ethylene and hydrogen sulfide.

Comparative Example

Example 2

A first mixture comprising a naphtha feed is provided, the naphtha feed having an atmospheric boiling range of 0.0° C. to 220° C. and (i) a hydrocarbon content of 99.8 wt. % and a total sulfur content (all reactive sulfur species—primarily mercaptans) of 0.2 wt. %, the weight percents being based on the weight of the naphtha feed. The naphtha feed is exposed to a temperature of 780° C. at a pressure of 1.3 bar (absolute) for a residence time of approximately 0.2 seconds. Steam cracking the naphtha feed under these conditions produces a second mixture comprising 30 wt. % $C_2$ unsaturates, 0.15 wt. % hydrogen sulfide, 35 ppmw methyl mercaptan, 12 ppmw total mercaptans, 50 ppmw thiophene, and 60 wt. % of $C_{3+}$. Following the steam cracking, the second mixture is exposed to a temperature$\leq 100.0°$ C., which lessens the amount of reversion mercaptans formation from, e.g., the reaction of the second mixture's ethylene and hydrogen sulfide.

Example 1 demonstrates that exposing the first mixture to a temperature$\geq 1.20 \times 10^{3\circ}$ C. under pyrolysis conditions converts $\geq 90.0$ wt. % of the first mixture's mercaptans to hydrogen sulfide, based on the weight of mercaptans in the first mixture. The example also demonstrates that the conversion produces a second mixture comprising $\geq 1.0$ wt. % $C_2$ unsaturates, $\leq 20.0$ wt. % $CO_N$, wherein $x \geq 1.0$ and $\leq 1.0$ ppmw thiophene based on the weight of the second mixture. Although a conventional pyrolysis process (steam cracking) does result in feed mercaptans conversion, a significant amount of the mercaptans (approximately 20%) is converted to undesirable refractory sulfur species such as thiophene and $C_{3+}$ sulfur species. In Example 1, the $C_{3+}$ comprise $\leq 10.0$ ppmw of sulfur-containing molecules based on the total weight of $C_{3+}$ in the second mixture. Other conventional pyrolysis processes, such as PDX, are capable of converting feed mercaptans, but produce an undesirably large amount of water and carbon dioxide.

All patents, test procedures, and other documents cited herein, including priority documents, are fully incorporated by reference to the extent such disclosure is not inconsistent and for all jurisdictions in which such incorporation is permitted.

While the illustrative forms disclosed herein have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside herein, including all features which would be treated as equivalents thereof by those skilled in the art to which this disclosure pertains.

When numerical lower limits and numerical upper limits are listed herein, ranges from any lower limit to any upper limit are contemplated.

The invention claimed is:

1. A hydrocarbon conversion process, comprising:
   (a) providing a first mixture comprising ≥0.5 wt. % hydrocarbon and ≥4.0 ppmw mercaptans based on the weight of the first mixture; and
   (b) exposing the first mixture to a temperature≥$1.20\times10^{3}$° C. in a first region under pyrolysis conditions and converting by pyrolysis at least a portion of the hydrocarbon, and ≥90.0 wt. % of the mercaptans in the first mixture based on the weight of the mercaptans in the first mixture, to produce a second mixture, the second mixture comprising ≥1.0 wt. % $C_2$ unsaturates, ≤20.0 wt. % $CO_x$, wherein x is 1 or 2, and ≤1.0 ppmw thiophene based on the weight of the second mixture.

2. The process of claim 1, wherein the first mixture comprises ≥20.0 wt. % methane and ≥10.0 ppmw methyl mercaptan based on the weight of the first mixture; the first mixture being obtained from a natural gas with no intervening mercaptan-removal steps, and wherein the second mixture comprises ≤0.05 ppmw methyl mercaptan based on the weight of the second mixture.

3. The process of claim 1, wherein the first mixture further comprises hydrogen sulfide in an amount in the range of 50.0 ppmw to 5 wt. % based on the weight of the first mixture.

4. The process of claim 1, wherein the first mixture is exposed to a temperature≥$1.45\times10^{3}$° C. during the pyrolysis.

5. The process of claim 1, wherein the second mixture further comprises hydrogen sulfide, and further comprising (c) separating hydrogen sulfide from the second mixture to produce a third mixture.

6. The process of claim 5, further comprising:
   (d) combining a first reactant and a second reactant in a second region to produce a fourth mixture, the first and second regions being at least partially coextensive; and
   (e) at least partially oxidizing the fourth mixture in the second region to produce a fifth mixture; wherein
      (i) the pyrolysis and the oxidizing occur at substantially different times, and
      (ii) at least a portion of the temperature of the first region during the pyrolysis is derived from the heat generated during the oxidizing in the second region.

7. The process of claim 6, wherein
   (i) step (e) further comprises oxidizing at least a portion of any combustible non-volatiles located in the first region; and
   (ii) the fifth mixture comprises ≤10.0 ppmw $SO_y$, y being in the range of from 2 to 4; the ppmw being based on the weight of the fifth mixture.

8. The process of claim 1, wherein ≥95.0 wt. % of the mercaptans in the first mixture are converted to non-thiophenic, non-mercaptan sulfur compounds during the pyrolysis.

9. The process of claim 1, wherein the second mixture comprises acetylene, and the process further comprises converting at least a portion of the acetylene in the second mixture to ethylene.

10. The process of claim 9, further comprising polymerizing at least a portion of the ethylene.

11. A methane conversion process, comprising:
    (a) providing a first mixture comprising ≥90.0 wt. % methane and ≥4.0 ppmw mercaptans based on the weight of the first mixture; and
    (b) exposing the first mixture under thermal pyrolysis conditions to a temperature sufficient for converting
       (i) ≥10.0 wt. % of the methane in the first mixture to unsaturated hydrocarbon based on the weight of the methane in the first mixture, and
       (ii) ≥90.0 wt. % of the mercaptans in the first mixture to non-mercaptan, non-thiophenic sulfur compounds based on the weight of the mercaptans in the first mixture
    to produce a second mixture comprising ≥1.0 wt. % $C_2$ unsaturates based on the weight of the second mixture.

12. The process of claim 11, wherein the first mixture further comprises ≥10.0 ppmw hydrogen sulfide based on the weight of the first mixture.

13. The process of claim 11, wherein (i) ≥90.0 wt. % of the mercaptans converted in step (b) are converted to hydrocarbon and hydrogen sulfide based on the weight of mercaptans converted in step (b), and (ii) ≤10.0 wt. % of the hydrogen sulfide in the second mixture reacts with the $C_2$ unsaturates in the second mixture, based on the weight of the hydrogen sulfide in the second mixture.

14. The process of claim 11, wherein the second mixture further comprises hydrogen sulfide, and further comprising separating hydrogen sulfide from the second mixture.

15. The process of claim 11, wherein the second mixture (i) comprises ≤1.0 ppmw methyl mercaptan based on the weight of the second mixture and (ii) has a $CO_x$:$C_2$ unsaturates molar ratio≤0.3, wherein x is 1 or 2.

16. The process of claim 11, wherein the second mixture comprises ≤2.0 wt. % $CO_x$, wherein x is 1 or 2, based on the weight of the second mixture.

17. The process of claim 11, wherein the exposing temperature is ≥$1.20\times10^{3}$° C.

18. The process of claim 11, wherein the exposing temperature is $1.40\times10^{3}$° C., and the thermal pyrolysis is conducted for a residence time≤0.05 seconds.

19. The process of claim 11, wherein the exposing temperature is ≥$1.60\times10^{3}$° C.

20. The process of claim 11, wherein the second mixture comprises ≤0.1 ppmw thiophene based on the weight of the second mixture.

21. A method for treating natural gas, comprising
    (a) providing a first mixture comprising ≥90.0 wt. % of natural gas, the natural gas comprising ≥1.0 wt. % methane, ≥1.0 ppmw hydrogen sulfide, and ≥4.0 ppmw mercaptans based on the weight of the natural gas;
    (b) exposing the first mixture under thermal pyrolysis conditions to a temperature sufficient for converting
       (i) ≥10.0 wt. % of the methane in the first mixture to unsaturated hydrocarbons and molecular hydrogen, based on the weight of the methane in the first mixture, and
       (ii) ≥90.0 wt. % of the mercaptans in the first mixture to non-mercaptan, non-thiophenic sulfur compounds based on the weight of the mercaptans in the first mixture, to produce a second mixture comprising ≥1.0 ppmw hydrogen sulfide and ≥1.0 wt. % $C_2$ unsaturates based on the weight of the second mixture; and
    (c) separating at least a portion of the hydrogen sulfide from the second mixture; wherein the natural gas is provided to the first mixture with no intervening mercaptan-removal steps.

22. The method of claim 21, wherein the natural gas comprises ≥50.0 ppmw mercaptans based on the weight of the natural gas.

23. The method of claim 21, wherein the natural gas comprises ≥50.0 ppmw hydrogen sulfide based on the weight of the natural gas.

24. The method of claim 21, wherein the exposing temperature is ≥$1.20 \times 10^3$° C.

25. The method of claim 21, wherein the second mixture (i) comprises ≤1.0 ppmw methyl mercaptan based on the weight of the second mixture and (ii) has a $CO_x:C_2$ unsaturates molar ratio≤0.3, wherein x is 1 or 2.

* * * * *